(12) United States Patent
Strannemalm

(10) Patent No.: US 8,003,846 B2
(45) Date of Patent: Aug. 23, 2011

(54) ABSORBENT ARTICLE COMPRISING ONE OR SEVERAL PATTERNS

(75) Inventor: Kenneth Strannemalm, Floda (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 11/812,446

(22) Filed: Jun. 19, 2007

(65) Prior Publication Data

US 2007/0250023 A1 Oct. 25, 2007

Related U.S. Application Data

(63) Continuation of application No. PCT/SE2004/001918, filed on Dec. 20, 2004.

(51) Int. Cl.
*A61F 13/15* (2006.01)
(52) U.S. Cl. ............... 604/361; 604/385.24; 604/385.25; 604/385.26; 604/385.27; 604/385.3; 604/386; 604/387
(58) Field of Classification Search .................. 604/361, 604/385.24, 385.25, 385.26, 385.27, 385.3, 604/386, 387, 396
See application file for complete search history.

(56) References Cited

U.S. PATENT DOCUMENTS

| | | | | |
|---|---|---|---|---|
| 2,335,190 A * | 11/1943 | Minich | ............... | 428/398 |
| 3,613,679 A * | 10/1971 | Bijou | ............... | 602/75 |
| 5,133,707 A * | 7/1992 | Rogers et al. | ............... | 604/389 |
| 5,190,812 A | 3/1993 | Joseph et al. | | |
| 5,200,247 A * | 4/1993 | Wu et al. | ............... | 428/131 |
| 5,897,541 A | 4/1999 | Uitenbroek et al. | | |
| 5,993,433 A | 11/1999 | St. Louis et al. | | |
| 6,142,968 A | 11/2000 | Pigg et al. | | |
| 6,810,811 B2 * | 11/2004 | Grounds et al. | ............... | 101/485 |
| 6,921,570 B2 * | 7/2005 | Belau et al. | ............... | 428/103 |
| 7,347,845 B2 * | 3/2008 | Zajaczkowski | ............... | 604/385.01 |
| 2003/0088224 A1 | 5/2003 | Ceman et al. | | |
| 2003/0144596 A1 * | 7/2003 | Tsubata | ............... | 600/500 |
| 2005/0119633 A1 * | 6/2005 | Zajaczkowski | ............... | 604/386 |
| 2005/0143699 A1 * | 6/2005 | Linder | ............... | 604/383 |
| 2006/0068168 A1 * | 3/2006 | Olson et al. | ............... | 428/152 |
| 2006/0246802 A1 * | 11/2006 | Hughes et al. | ............... | 442/327 |

FOREIGN PATENT DOCUMENTS

| | | | |
|---|---|---|---|
| EP | 1 147 755 A2 | 10/2001 | |
| JP | 6464823 A | * | 3/1989 |
| JP | 3-75056 A | | 3/1991 |
| JP | 3-58416 U | | 6/1991 |

(Continued)

OTHER PUBLICATIONS

PCT/ISA/210.

(Continued)

*Primary Examiner* — Jacqueline F. Stephens
(74) *Attorney, Agent, or Firm* — Buchanan Ingersoll & Rooney PC

(57) ABSTRACT

An absorbent article for disposable use having at least one pattern (118) in the form of a text, image or the like. A background layer (146) and at least one intermediate layer (147) are arranged behind the pattern (118), in conjunction with which the intermediate layer or layers (147) exhibits or exhibit a first, essentially transparent state, and in conjunction with which the intermediate layer or layers (147) is or are transformed into a second, more opaque state when it or they is or are stretched.

20 Claims, 10 Drawing Sheets

FOREIGN PATENT DOCUMENTS

| | | | |
|---|---|---|---|
| JP | 10-506586 A | | 6/1998 |
| JP | 2001106984 A | * | 4/2001 |
| JP | 2004-121363 A | | 4/2004 |
| RU | 2203010 | | 5/2002 |
| WO | WO 96/10380 A2 | | 4/1996 |
| WO | 96-31175 A | | 10/1996 |
| WO | WO 9851247 A1 | * | 11/1998 |
| WO | WO03022730 A1 | * | 3/2003 |
| WO | WO 2005053588 A1 | * | 6/2005 |

OTHER PUBLICATIONS

PCT/ISA/237.

Disposable diapers. Expert's opinion, 2003, http://www.mamajournal.ru/grudnichok/mooni.html Oct. 9, 2008.

A.K. Faizulin et al., Nursing articles: disposable diapers—professionals' opinion, 2001, http://www.parenting.ru/s.php/29.htm, Oct. 9, 2008.

M. Kamat et al., Disposable diapers: a hygienic alternative, Indian J Pediatr., Nov. 2003 70(11), p. 879-881.

Translation of Official Decision of Grant dated Feb. 27, 2009 in corresponding Russian patent Application No. 2007127669 with English translation.

* cited by examiner

ABSORBENT ARTICLE COMPRISING ONE OR SEVERAL PATTERNS

CROSS-REFERENCE TO RELATED APPLICATIONS

The present application is a continuation of PCT/SE2004/001918, filed on Dec. 20, 2004, and which designates the U.S. The entire contents of PCT/SE2004/001918 are incorporated herein by reference.

TECHNICAL FIELD

The invention relates to an absorbent article for disposable use comprising at least one pattern, in conjunction with which the pattern is superimposed on a background layer.

BACKGROUND

In the case of absorbent articles such as diapers, sanitary towels, incontinence protection, etc., the application of patterns in the form of texts, images, symbols or the like to certain layers included in the article is previously disclosed. Combinations comprising at least two of the pattern forms are also encountered. The texts and the symbols are preferably of an informative nature, for example in the form of a user instruction, a warning text or product information such as a size indication. The images are preferably in the form of decorative patterns, product information or user instructions. Patterns in the form of trademarks and/or company logotypes are also commonly encountered.

The pattern is usually arranged on one of the layers that forms the outside of the article when it is used, for example on the front or the rear end part of the article, on fastening tabs or on a side panel. It is especially common for the pattern to be arranged on the outside of the article on or close to the waist area of the article.

The pattern sometimes relates to instructions in respect of how the article must be applied to the wearer, the suitable article size for a certain body weight and the like.

Such patterns are commonly positioned together with other types of pattern such as a distinctive product mark, purely decorative patterns, positioning indicators for example for attachment flaps, indicators to show which end of the article must be positioned towards the front on the wearer, and so on.

The articles thus comprise different types of patterns, some intended to inform the user about handling the article, some simply intended to make the article more visually attractive, and some intended to warn of incorrect handling.

Certain patterns, intended to warn of incorrect handling which may be associated with a risk, such as a warning of the risk of suffocation if a child places a baby's diaper over its head, must naturally be capable of being read by a parent before the incorrect handling occurs.

Certain other patterns inform of less serious incorrect handling, such as information to the effect that the size of the article is incorrect in relation to the body size of the wearer, that the attachment flaps have been tightened too tightly around the wearer's waist or the like. This type of information does not need to be made visible until the incorrect use has taken place, in conjunction with which the incorrect use can be corrected directly or on the next occasion that an absorbent article is changed on the wearer, or even on the next occasion on which new absorbent articles are purchased.

Indicators for demonstrating the excessive stretching of a layer of material are described in PCT document WO 96/31175. The document describes a layer of material comprising a pattern consisting of curved lines when the layer of material is not stretched. The curved lines face in the intended direction of stretching. When the layer of material is stretched, the radii of curvature of the lines increase, in conjunction with which the initially curved lines become straighter, in conjunction with which the curvature of the lines gives an indication of by how much the layer of material has been stretched.

One disadvantage associated with the solution in WO 96/31175 is that the curved lines, regardless of whether or not overstretching has occurred, are always visible on the absorbent article. Patterns which are always visible on the absorbent article must naturally exhibit a certain degree of harmony with other patterns on the article, for which reason the warning signal cannot be executed sufficiently clearly and distinctly. A very clear and distinct warning signal runs the risk of dominating the pattern of the article in relation to other patterns that it is wished to emphasize on the article.

Another disadvantage is that the user must understand the symbols in the form of curved lines, and must also understand what it means when the curvature of the initially curved lines is changed and the level of change at which excessively high stretching of the layer of material has been reached.

If the layer of material is elastic, or if the layer of material is attached to an elastic layer of material, a third problem arises because the curvature of the curved lines essentially reverts to the original curvature when stretching of the layer of material ceases. This means that it is not possible to perform a verification in order, for example, to investigate whether the absorbent article has been tightened too tightly around the wearer's waist.

OBJECTS AND SUMMARY

Prior to the present invention, a need accordingly existed for an improved absorbent article, in which patterns intended to warn of minor errors in conjunction with the use of the absorbent article, such as the incorrect choice of article size, excessive tensioning around the waist, or the like, only become visible in conjunction with the incorrect use.

The need also existed for an improved absorbent article, in which the inspection of any errors can be read off both during and after use of the article.

The need existed, furthermore, for an improved absorbent article, in which the warning signal can be made more conspicuous.

Certain patterns are intended to be read and observed before use, in conjunction with which the patterns can comprise handling instructions, for example, which are only required in conjunction with putting the absorbent article on the wearer. Once the article has been put on the wearer, the presence of these patterns on the article is no longer either necessary or desirable.

Patterns of a certain type are, from the manufacturer's point of view, desirable to apply to the absorbent article, although they may be undesirable on the part of the wearer when the article is being worn. Examples of such patterns are trademarks for incontinence protection products, which the wearer does not wish to be visible through thin items of clothing, because these patterns reveal the wearer's incontinence problem.

In order to solve the problem of rendering a pattern invisible, the arrangement of the pattern on a separate layer that is detachably attached to the article is previously disclosed. A user looks at the pattern and reads the information before use, after which he/she removes the separate layer containing the pattern.

A product of this kind is described in US 2003/0088224 A1. Although the pattern is certainly removed by this process, the problem remains, namely that the removed layer has formed a separate residual product which must be dealt with. The wearer must then either find a suitable place to dispose of the layer or, in the absence of such a place, must keep the layer until such a place is found.

A need accordingly existed for an improved absorbent article, where the wearer can read a text or look at an image on the article before use, and where the text or the image is essentially rendered invisible when it is being worn.

An absorbent article of the kind mentioned in the introduction has been achieved, in conjunction with which the pattern essentially overcomes the problems referred to by way of introduction that have been associated with previous articles of this kind.

An absorbent article executed in accordance with the invention is characterized first and foremost in that at least one layer of material is arranged between the pattern and the background layer, in conjunction with which the intermediate layer or layers exhibits or exhibit a first, essentially transparent state, and in conjunction with which the intermediate layer or layers is or are transformed by elongation into a second, more opaque state.

In accordance with one embodiment of an absorbent article in accordance with the invention, the pattern and the background layer exhibit essentially the same shade of colour, in conjunction with which the pattern is essentially invisible against the background layer through the intermediate layer or layers when the intermediate layer or layers exhibits or exhibit the first, essentially transparent state, and in conjunction with which the pattern and the intermediate layer or layers exhibit an essentially different shade of colour when the intermediate layer or layers exhibits or exhibit the second, essentially opaque state, in conjunction with which the pattern is essentially visible against the intermediate layer or layers.

In accordance with another embodiment of an absorbent article in accordance with the invention, the pattern and the background layer exhibit essentially different shades of colour, in conjunction with which the pattern is essentially visible against the background layer through the intermediate layer or layers when the intermediate layer or layers exhibits or exhibit the first, essentially transparent state, and in conjunction with which the pattern and the intermediate layer or layers exhibit essentially the same shade of colour when the intermediate layer or layers exhibits or exhibit the second, essentially opaque state, in conjunction with which the pattern is essentially invisible against the intermediate layer or layers.

In accordance with one embodiment, the background layer consists of one or other of the liquid-permeable covering layer or backing layer of the article.

One embodiment of the invention is characterized in that the pattern is arranged directly on the intermediate layer, in conjunction with which the pattern is arranged on the side of the aforementioned intermediate layer that faces away from the background layer.

In accordance with one embodiment of an absorbent article in accordance with the invention, the pattern is arranged on a separate pattern layer, in conjunction with which the pattern layer is essentially transparent both before and after elongation.

In accordance with one embodiment, the intermediate layer or layers and the pattern layer are laminated together and constitute a prefabricated label.

In accordance with another embodiment, the prefabricated label contains a background layer.

In accordance with one embodiment, the intermediate layer or layers is or are attached to an elasticated surface of the article, in conjunction with which the intermediate layer or layers is or are elongated automatically when the surface to which the layer or layers is or are attached is elongated.

One embodiment relates to an absorbent article in which the intermediate layer or layers is or are arranged in the elasticated waist part of the absorbent article.

Another embodiment relates to an absorbent article in which the intermediate layer or layers is or are arranged on the elasticated belt of the absorbent article, in conjunction with which the intermediate layer or layers is or are elongated automatically when the belt is elongated.

In one embodiment, the intermediate layer or layers is or are arranged on at least one of the elasticated attachment flaps of the absorbent article, in conjunction with which the intermediate layer or layers is or are elongated automatically when the attachment flaps are elongated.

In accordance with one embodiment, the intermediate layer or layers contracts or contract when the surface on which the intermediate layer or layers is or are arranged contracts.

One embodiment relates to an absorbent article in which the intermediate layer or layers is or are intended to be elongated manually in order to cause the intermediate layer or layers to be changed from the first, essentially transparent state to the second, more opaque state.

In accordance with one embodiment, the intermediate layer or layers exhibits or exhibit a combined opacity of not more than 70.5% in accordance with the method described in ISO 2471:1988 when the intermediate layer or layers is or are in the first state.

In accordance with one embodiment, the intermediate layer or layers exhibits or exhibit a combined opacity of at least 76.2% in accordance with the method described in ISO 2471:1988 when the intermediate layer or layers has or have been transformed into the second state.

In accordance with one embodiment, changing the intermediate layer or layers from the first state to the second state is achieved by elongating the layer or layers of material by 10-200%.

In accordance with one embodiment, an absorbent article for disposable use comprises at least one pattern of a color, the pattern superimposed on a background layer having essentially a same shade of color as the at least one pattern, and at least one layer arranged over the background layer, the at least one layer exhibits a first, essentially transparent state in a first mode. The at least one layer is caused by elongation to be transformed into a second essentially opaque state in a second mode.

In accordance with one embodiment, an absorbent article for disposable use comprises at least one pattern of a color arranged on a surface of a pattern layer, the pattern layer including an intermediate layer and being superimposed on a background layer having a different shade of color than the color of the at least one pattern, the pattern layer exhibiting a first, essentially transparent state in a first mode in which a color of the pattern layer is different than the color of the at least one pattern. The pattern layer is caused by elongation to be transformed into a second state in a second mode in which the color of the pattern layer is essentially the same as the color of the at least one pattern.

In accordance with one embodiment, an absorbent article for disposable use comprises a top layer having a pattern of a color on it, a background layer of the same color as the pattern, wherein the pattern is superimposed on the background layer, and optionally, a third layer arranged between the top layer and the background layer. At least one of the top and third layers exhibits a first, essentially transparent state in a first mode, and the at least one of the top and third layers is caused by elongation to be transformed into a second essentially opaque state in a second mode. The transformation of the at least one of the top and third layers affects the readability of the pattern.

BRIEF DESCRIPTION OF THE DRAWINGS

The invention is described in more detail below with reference to the accompanying Figures.

DESCRIPTION OF THE PREFERRED EMBODIMENTS

Figure 1A:
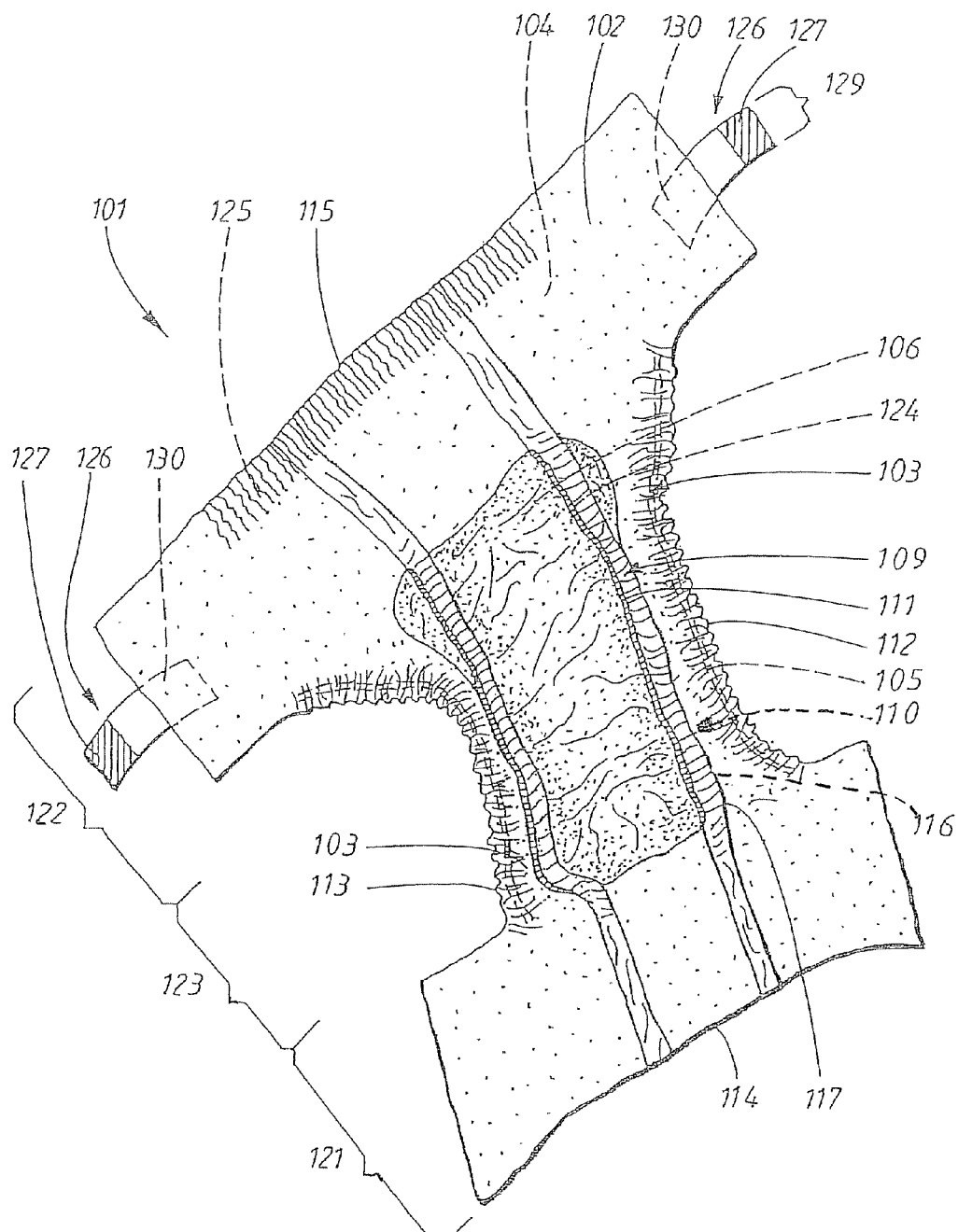
FIG. 1a shows an open diaper in accordance with an embodiment of the invention from the side that is intended to face towards the wearer when it is being worn.

The embodiment of the invention is an absorbent article for disposable use, which exhibits a pattern that emerges only after a certain event has taken place. An example of an event is that some part of the article was tensioned too tightly against the wearer when the article was put on, in conjunction with which the pattern comprises a warning in the form of an image, a symbol, a text or the like.

Another embodiment of the invention is an absorbent article for disposable use which exhibits a pattern, for example in the form of a text, image or symbol, which is visible to an observer on the outside of the article, and which, after a certain event, becomes less visible or even invisible. For example, a well-known trademark for incontinence diapers is rendered invisible, at least partially, when the article is put onto the wearer.

Absorbent articles include absorbent articles of the type such as all-in-one diapers, pant diapers, belt diapers or sanitary protection of the panty type, that is to say articles which enclose the wearer's abdomen when they are being worn. It is naturally also possible to apply the invention to less absorbent products such as sanitary towels, panty liners or light incontinence protection intended to be positioned in the crotch of a wearer. The design and positioning of these articles in a wearer's undergarments nevertheless means that the arrangement in accordance with the invention is probably less applicable for these types of absorbent articles.

All-in-one diapers, pant diapers or belt diapers may consist of baby's diapers intended for infants who are not yet potty trained, or of incontinence protection intended for adult incontinent wearers.

So-called pant diapers are characterized above all in that they have already been folded at the time of manufacture about an essentially transverse fold, line in the crotch area of the pant diaper and have subsequently been joined together at the waist. Diapers of this type are intended to be applied to a wearer like a pair of underpants, that is to say they are passed over the wearer's legs. The joint in the waist area of the pant diaper is usually capable of separation, in conjunction with which the pant diaper can be removed after use without having to be passed all the way down over the wearer's feet when it is to be removed. This possibility is particularly appreciated when the pant diaper is smeared with faeces after use.

Belt diapers are characterized in that they comprise a transverse belt in relation to the absorbent part of the diaper attached to either the front or the rear transverse edge of the diaper.

In conjunction with the application of a belt diaper of this kind, the belt is fixed in a first stage around the wearer's waist. The absorbent part of the diaper thus hangs loosely from the belt. The absorbent part of the diaper is then passed between the wearer's legs and is attached to the belt, in conjunction with which the belt includes fixing surfaces intended to adhere to fixing devices arranged on the absorbent part of the diaper adjacent to its free transverse edge.

So-called all-in-one diapers are characterized in that they include attachment flaps, by means of which the front and rear waist part of the diaper are attached when the diaper is applied around the waist of a wearer.

FIG. 1a shows essential components of a diaper 101 in accordance with an embodiment of the invention.

The diaper 101 is an open diaper of the so-called all-in-one type. The diaper 101 is not joined together in the waist area when it is sold, but is intended instead to be applied around a wearer's abdomen, in order thereafter to be joined together around the wearer's waist. This type of diaper 101 is commonly encountered for both infant and adult incontinent wearers.

The diaper 101 is essentially in the form of an hourglass and as such exhibits longitudinal edges 112, 113, a front transverse edge 114 and a rear transverse edge 115. The diaper 101 also exhibits a front edge part 121, a rear edge part 122 and a narrower crotch part 123 situated between the end parts 121, 122. The crotch part 123 is intended to be situated in the narrowest area between the wearer's thighs when it is being worn.

When wearing the diaper 101, the front part of the crotch part 123 and the front end part 121 function principally as a receiving area for urine, while the rear part of the crotch part 123 and the rear end part 122 function-principally as a receiving area for faeces.

The diaper 101 comprises a liquid-permeable covering layer 102 arranged over the surface of the diaper 101 that is intended to face towards the wearer when it is being worn, a backing layer 104 arranged over the surface of the diaper that is intended to face away from the wearer when it is being worn, an absorption body 106 enclosed between the liquid-permeable covering layer 102 and the backing layer 104, and side flaps 103 arranged outside the absorption body 106.

The liquid-permeable covering layer 102 of the diaper 101 extends outside the absorption body 106 around the periphery of the entire absorption body 106. The liquid-permeable covering layer 102 can consist of any material that is suitable for the purpose. Examples of commonly encountered liquid-permeable covering materials are non-woven textile materials, known as nonwoven materials, perforated plastic films, meshes made of plastic or textile, and liquid-permeable foam layers. Liquid-permeable covering materials that are made of continuous thin fibres which extend predominantly in the longitudinal or transverse direction of the article are also encountered. Laminates consisting of two or more of the above-mentioned possible covering materials are also commonly encountered, as are coverings consisting of different materials in different parts of the surface.

A situation commonly encountered today is that the liquid-permeable covering layer 102 consists of a fully or partially elastic material in order to provide the diaper 101 with a better fit when it is being worn.

Diapers 101 containing absorption bodies 106 which exhibit especially high strength and resistance to wear may even function without the need to provide any extra liquid-permeable covering layer on that side of the diaper 101 that faces towards the wearer when it is being worn.

The backing layer 104 also extends beyond the absorption body 106 around the periphery of the entire absorption body 106. Backing layers 104 that are normally present on diapers 101 are usually liquid-impermeable, although other types of backing layer are encountered. The backing layer 104 can consist of a range of different materials. The backing layer 104 most commonly consists of a thin liquid-impermeable plastic film, although it is also possible to use other types of liquid-impermeable material, such as nonwoven materials that have been made liquid-impermeable for example by means of plastic coating, liquid-impermeable foam layers, liquid-impermeable adhesive or similar. The backing layer 104 can also consist of a liquid-impermeable, vapour-permeable material. Also encountered are laminates containing at least one liquid-impermeable layer arranged against the absorption body 106. These laminates usually consist of a liquid-impermeable material functioning as a moisture barrier and a more textile-like material arranged on the side of the diaper 101 that faces away from the wearer when it is being worn, as a consequence of which the outside of the diaper 101 more closely resembles an item of clothing when it is being worn. The textile-like layer of the laminate usually consists of a nonwoven layer, in conjunction with which the nonwoven layer can be executed so that it functions as a receiving material for a hook-and-loop material of the male type. A nonwoven material of this kind is characterized in that it comprises closed eyes, so-called loops, or the like.

The liquid-permeable covering layer 102 and the backing layer 104 are attached to one another outside the absorption body 106 along the entire periphery of the absorption body 106.

The liquid-permeable covering layer 102 and the backing layer 104 may be attached to one another by a number of different means. Examples of means of attachment include gluing, thermal fusion, ultrasonic welding or the like.

Elastic devices 105 are arranged outside the absorption body 106 in those parts of the side flaps 103 of the diaper 101 which run essentially in the longitudinal direction of the diaper 101. The elastic devices 105 function as leg elastic and have the task of preventing liquid and faeces from leaking out past the longitudinal edges 112, 113 of the diaper 101, and in this way they form outer moisture barriers 108 together with surrounding layers. The elastic devices 105 consist of one or more elastic threads that have been applied in their stretched state between the liquid-permeable covering layer 102 and the backing layer 104, at least in the crotch part 123 of the diaper 101. The elastic devices 105 are attached to the backing layer 104 and the covering layer 102 by gluing, ultrasonic welding or the like.

In alternative embodiments, the elastic devices can be arranged on the side of the side flaps 103 that is intended to face towards the wearer when it is being worn, or on the opposite side of the side flaps, and as such they are naturally only attached to the covering layer 102 and the backing layer 104 respectively.

The elastic devices can, in alternative embodiments, consist of elastic tape material, for example made of a foam material.

The hourglass-shaped absorption body 106 can be constructed from one or more layers of cellulose fluff pulp. The cellulose fluff pulp can be mixed for this purpose with fibres or particles of a high-absorbency polymer material of the kind which, in conjunction with absorption, chemically bonds large quantities of liquid to form a liquid-containing gel. The absorption body 106 can also contain high-absorbency polymer material arranged in a layer inside the absorption body or in conjunction with the surface or surfaces of the absorption body. Additional components to improve the characteristics of the absorption body 106 can also be present in the absorption body 106. Examples of such components include binding fibres, different types of liquid-distributing layers or fibres, form-stabilizing components, reinforcing fibres or the like. The absorption body 106 can naturally also consist of other types of absorption material, such as absorbent nonwoven material, absorbent foam, textile materials, peat or mixtures of different kinds of absorption material.

Special layers with the ability rapidly to receive quite large quantities of liquid and to retain this liquid temporarily, in order subsequently to release the temporarily stored liquid to different parts of the absorption body 106, can also be included in diapers of the prescribed kind. Such receiving layers are normally arranged for this purpose between the liquid-permeable covering layer 102 of the diaper 101 and the absorption body 106. No receiving layer is shown in FIG. 1.

In order further to prevent liquid or faeces from leaking out via the side edges 112, 113 of the diaper 101, the diaper 101 is provided with inner side leakage barriers 109 on the side that is intended to face towards the wearer when it is being worn. The inner side leakage barriers 109 are arranged adjacent to the longitudinal edges 110 of the absorption body 106 and extend essentially in the longitudinal direction of the diaper 101. The respective inner side leakage barrier 109 is executed from a separate material strip 111, which exhibits two essentially parallel longitudinal edges 116, 117. The material strip 111 is double-folded, in conjunction with which the longitudinal edges 116, 117 of the material strip 111 are arranged adjacent to one another. The edges 116, 117 of the material strip 111 are attached to the covering layer 102 and constitute the attached edge of the inner side leakage barrier. The folded edge of the material strip 111 constitutes the free edge of the inner side leakage barrier 109.

The inner side leakage barriers 109 are folded down and attached to the covering layer 102 on the front end part 121 and the rear end part 122 of the diaper 101. The inner side leakage barriers 109 comprise elastic elements 124 attached to the inner side leakage barriers 109 in their pre-tensioned state. The elastic elements 124 are conveniently arranged adjacent to the free edges of the inner side leakage barriers 109. When the pre-tensioned elastic elements 124 are released, they contract together with the free edges of the inner side leakage barriers 109, thereby causing the inner side leakage barriers 109 to be brought into a raised configuration remote from the liquid-permeable covering layer 102, at least, in the crotch part 123 of the diaper 101, where the side leakage barriers 109 are not folded down and attached to the covering layer 102.

The rear and/or front parts of the diaper 101 can also be provided with so-called waist elastic 125, which consists of elastic devices arranged along the front transverse edge 114 and/or the rear transverse edge 115 of the diaper 101 in order to provide the diaper 101 with a soft and pliable closure around the wearer's waist. In the illustrative embodiment described here, only the rear end part 122 of the diaper 101 is provided with waist elastic 125. In the example shown here, the waist elastic 125 consists of a thin strip of elastic foam material, which is attached by means of adhesive between the backing layer 104 and the liquid-permeable surface layer 102. The waist elastic 125 is applied in its stretched state between the layers 102, 104 in order to bring about a holding force which stretches the diaper 101 around the wearer's waist.

Two soft and inelastic attachment flaps 126 are arranged on the rear end part 122 for the purpose of securing the diaper 101 around a wearer. One attachment flap 126 is arranged for this purpose on each side part of the rear end part 122. The attachment flaps 126 connect the rear end part 122 to the front end part 121 when it is being worn by the attachment flaps 126 exhibiting fixing devices 127, which can be attached to a receiving part arranged on the front end part 121 of the diaper 101. The attachment flaps 126 are appropriately executed from a very soft and inelastic material, for example from a single nonwoven layer or a laminate.

The attachment flaps may be elastic in alternative embodiments.

The fixing devices 127 preferably consist of male parts of a hook-and-loop material and are attached to the attachment flaps 126, for example with adhesive, on the side of the attachment flaps 126 which faces towards the receiving part of the diaper 101 when it is being worn.

The receiving part, which is not shown in FIG. 1, for the attachment flap 126 consists of a strip of a receiving material adapted for the fixing device 127 of the attachment flap 126. The receiving part extends essentially parallel to the front transverse edge 114 of the side of the diaper that faces away from the wearer when it is being worn, that is to say on the side of the backing layer 104 that faces away from the absorption body 106. In the illustrative embodiment described here, the material in the receiving part consists of a female part of a hook-and-loop material and is appropriately executed so that its extent in the longitudinal direction of the diaper 101 corresponds to the width 129 of the attachment flaps 126. The receiving part extends substantially over the width of the entire diaper 101 in the transverse direction of the diaper 101.

In alternative embodiments of a diaper, it is possible to consider the arrangement of separate receiving parts for the respective fixing devices 127, in which case the receiving parts are arranged in conjunction with the longitudinal edges 112, 113 of the diaper on the front transverse edge 114 of the diaper 101.

When putting the diaper 101 on an infant, the diaper 101 is placed between the infant's legs in the infant's crotch. The diaper 101 is then closed around the infant's waist by causing the attachment flaps 126 to overlap the front end part 121 so that the fixing devices 127 of the attachment flaps 126 can be applied to the receiving part in order to hold the diaper in place.

The attachment flaps 126 are attached to the rear end part 122 in the attachment areas 130 that are positioned in the areas of the rear end part 122 which lie next to the lateral edges 112, 113 running in the longitudinal direction. The attachment areas 130 consist of parts of the attachment flaps 126 and those parts of the rear end part 122 that are attached to one another.

The fixing devices 127 of the attachment flaps 126 in alternative embodiments can consist of a pressure-sensitive adhesive, in which case the receiving part (not shown in FIG. 1) consists of a material to which the selected pressure-sensitive adhesive of the fixing devices 127 can be attached so as to achieve the appropriate joint strength. Combinations of materials are usually selected so that the attachment between the fixing devices 127 and the receiving part can be opened and reclosed to allow the diaper 101 to be checked while it is being worn.

In alternative embodiments, the backing layer 104 can be adapted in such a way as to interact with the fixing devices 127 of the attachment flaps 126, in which case no special receiving part is required.

Figure 1B:
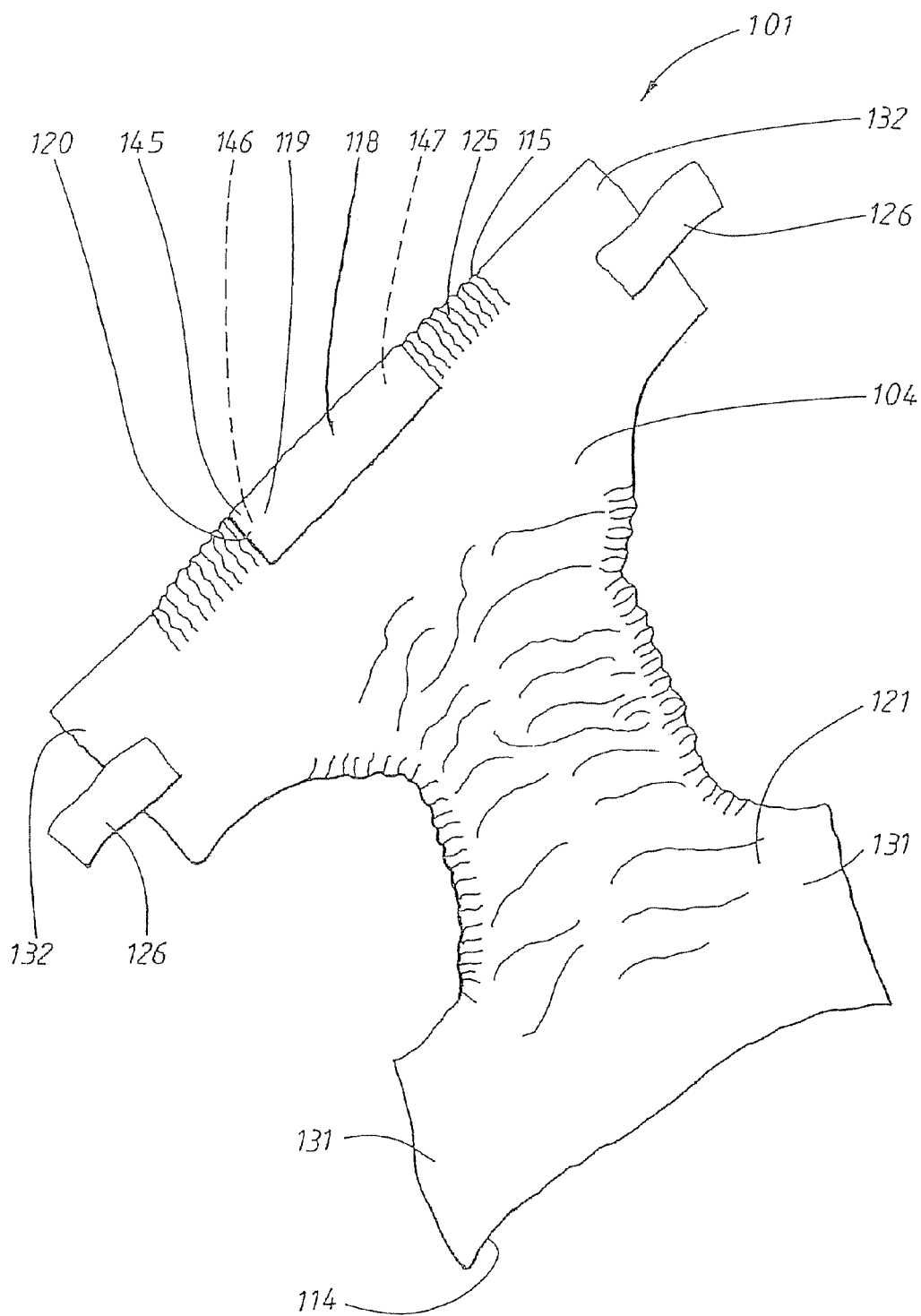
FIG. 1b shows the diaper in accordance with FIG. 1a before it has been worn, viewed from the side that is intended to face away from the wearer when it is being worn.

The diaper 101 is shown in FIG. 1b from the side that is intended to face away from the wearer when it is being worn, in conjunction with which the diaper 101 is shown before it was worn, or after having been worn by a wearer with a body size to which the diaper 101 is adapted.

The diaper 101 comprises a label 119 comprising three material layers. The three material layers consist of a transparent pattern layer 145 arranged outermost, furthest away from the diaper 101, a background layer 146 arranged innermost, closest to the diaper 101, and an intermediate layer 147 arranged between the pattern layer 145 and the background layer 146. A pattern 118 is arranged on the transparent pattern layer 145, in conjunction with which the pattern 118 is superimposed on the intermediate layer 147 and the background layer 146.

The diaper 101 is characterized first and foremost in that the intermediate layer 147 of the label 119 is essentially transparent in a first state, in conjunction with which the pattern 118 is essentially invisible against the background layer 146 through the transparent intermediate layer 147, because the background layer 146 and the pattern 118 exhibit essentially the same shade of colour. When the intermediate layer 147 is subjected to elongation, the intermediate layer 147 is transformed into a second, essentially less transparent state, in conjunction with which the pattern 118 stands out against the intermediate layer 147.

When the diaper 101 is put on a wearer, the diaper 101 is stretched around the wearer's waist when the attachment flaps 126 of the diaper 101 are attached to the front edge part 121 of the diaper 101. The waist elastic 125 of the diaper 101 is stretched out in conjunction with this from its initially contracted state, in conjunction with which the label 119 is elongated together with the waist elastic 125.

If the intermediate layer 147 of the label 119 is elongated too much in conjunction with putting the diaper 101 on a wearer, the intermediate layer 147 will be transformed into its second state, in conjunction with which the second state exhibits essentially less transparency compared with the first, non-elongated state. The background layer 146 is thus essentially concealed by the intermediate layer 147, in conjunction with which the intermediate layer 147 provides a new background for the pattern 118.

The result is that the pattern 118 becomes visible against the intermediate layer 147, which does not exhibit the same shade of colour as the shade of colour of the pattern 118.

If the diaper 101 is of the right size and is not tensioned too tightly around the wearer's waist, the intermediate layer 147 of the label 119 will remain transparent, in conjunction with which the pattern 118 will not be visible either during or after wearing of the diaper 101.

Figure 1C:
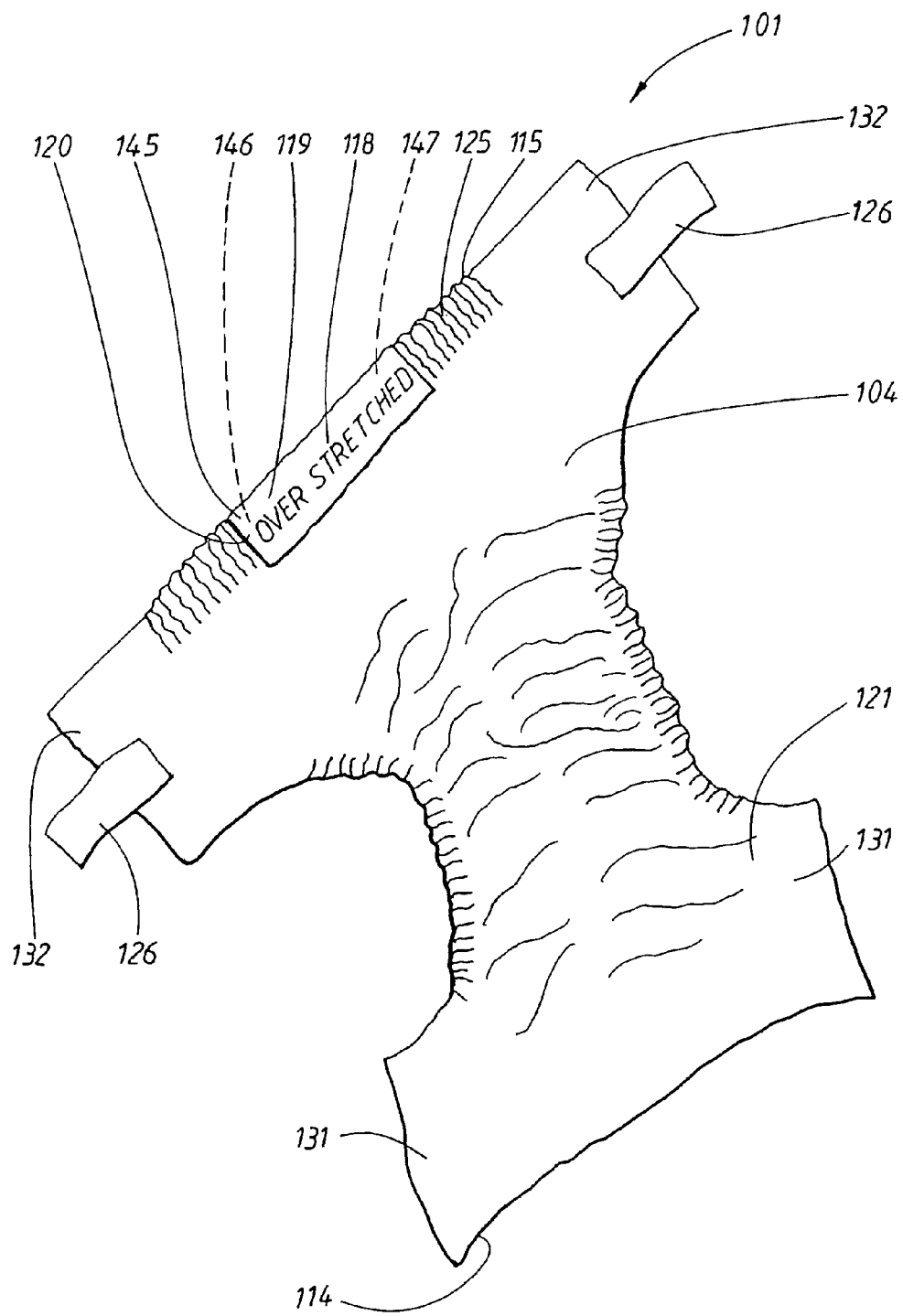
FIG. 1c shows the diaper in accordance with FIG. 1b after it has been worn and has been stretched too tightly around the wearer's waist, viewed from the side that is intended to face away from the wearer when it is being worn.

FIG. 1c shows a diaper 101 from the side that is intended to face away from the wearer when it is being worn, in conjunction with which the diaper 101 is shown after it has been worn and the diaper 101 has been stretched too tightly around the wearer's waist.

The diaper 101 may have been stretched too tightly around the wearer's waist for a number of different reasons, although one of the most common reasons is that the diaper 101 is too small in relation to the wearer (the infant or the incontinent patient). Another commonly encountered reason is that the person who carried out the diaper change (the care staff or the parent) tensioned the diaper 101 too tightly around the waist in the belief that this may reduce the risk of leakage or urine or faeces from the diaper 101.

A pattern 118 in the form of the words "OVER STRETCHED" can now be read on the label 119, because the intermediate layer 147 has been transformed into its second, essentially opaque state, in conjunction with which a colour contrast in relation to the pattern 118 has been achieved in conjunction with putting on the diaper.

The pattern 118 provides a warning message to the carer/parent and informs them if the diaper has been stretched unnecessarily tightly around the wearer's waist.

The pattern 118 can, in alternative embodiments, consist of an alternative warning text, a warning message in the form of an illustrative figure, symbol or the like. For example, information about the desirability of obtaining a larger size of diaper 101 may be revealed when the diaper 101 has been over stretched in the waist area.

The pattern 118 can, in other alternative embodiments, comprise a combination of images, text and symbols.

The label 119 is discreetly executed and exhibits no visible pattern before use or after correct use on a wearer with a body size to which the diaper 101 is adapted.

The label 119 exhibits a rectangular form and is arranged in conjunction with the rear transverse edge 115 of the diaper 101 with its long sides parallel to the rear transverse edge 115. Both end areas 120 of the label 119 are attached to the backing layer 104 of the diaper 101 by means of ultrasonic welding, although in alternative embodiments they can be attached by means of gluing, thermal welding or the like.

The means by which the label 119 has been attached to the diaper 101 is not critical for the invention, although it is important to avoid a method of attachment which physically influences the label 119 in such a way that the intermediate layer 147 is caused to be transformed fully or partially from its first state to its second state by handling during attachment to the backing layer 104 of the diaper 101.

It is also important for the label 119 to be attached to the diaper 101 in such a way that it is possible to stretch it sufficiently for the intermediate layer 147 to be capable of being transformed from its first, essentially transparent state into its second, at least partially opaque state. The intermediate layer 147 must, therefore, at the time when it is applied to the diaper 101, be in its first, essentially transparent state and must remain so, at least until the diaper 101 is to be put on a wearer.

The label 119 with its associated pattern 118 is arranged, in the embodiment described here, on the rear transverse edge 115 of the diaper 101 adjacent to the waist elastic 125.

In alternative embodiments, the label 119 comprising the pattern 118, which will become visible in the event of excessively high contact force against the wearer's body, can be positioned in some other elasticated zone of the diaper 101. Suitable positions include areas of the diaper 101 that are stretched automatically in connection with wearing the diaper.

Examples of alternative positions include on the front side panels 131 or the rear side panels 132 of the diaper 101 in those cases in which these exhibit elastic characteristics.

Another conceivable position is on the attachment tabs 126 of the diaper 101, in those cases in which these are elastic.

It is naturally also possible for the label 119 containing the pattern 118 to be positioned on the front end part 121 of the diaper adjacent to the front transverse edge 114 of the diaper 101, if the diaper 101 exhibits elastic characteristics at the front transverse edge 114.

Excessive tightening of the diaper 101 against the wearer's groin is a common occurrence. In order to indicate such excessively tight tensioning, it is appropriate to arrange labels 119 in accordance with the invention adjacent to the elastic devices 105 on the side flaps 103 of the diaper 101 and/or on the inner side leakage barriers 109 adjacent to the elastic elements 124. These labels 119 are difficult/impossible to inspect while the diaper is being worn, and inspection must accordingly be performed in conjunction with changing the diaper 101.

In order to prevent the label 119 that is arranged on the waist elastic 125 of the diaper 101 from becoming loose and baggy if the waist elastic 125 contracts after the initial elongation in conjunction with putting on the diaper 101, it is preferable to design the label 119 with elastic characteristics. It is possible, for example, to cause at least one of the layers 145, 146, 147 to be executed from an elastic material and to laminate the layers 145, 146, 147 together, in which case the label 119 will have elastic characteristics.

In an alternative embodiment, the layers 145, 146, 147 of the label 119 can be laminated together with the backing layer 104 over the waist elastic 125, in conjunction with which the label 119 is able to contract together with the waist elastic 125.

The intermediate layer 147 of the label 119 consists of a plastic film which is transformed from being transparent to become white and at least partially opaque when it is subjected to visco-elastic elongation.

It is a well-known fact that certain plastic materials change colour and become white when they are subjected to visco-elastic elongation.

The transition of the intermediate layer 147 from its first, essentially transparent state to its second, at least partially opaque state is irreversible and is caused by plastic deformation of the intermediate layer 147. The change in opacity is brought about by the formation of micro pores or cavities in the intermediate layer 147 when it undergoes plastic deformation, such as stretching, as a consequence of the presence in the intermediate layer 147 of fillers in the form of solid particles which are not elongated with the rest of the material. These micro pores or cavities mean that the light is refracted and that a large proportion of the incident light is reflected instead of passing through the layer. Alternatively, it is also conceivable to provide the intermediate layer 147 with micro ampoules containing a pigment. The micro ampoules will be caused to rupture by elongating the material, and the pigment will stain the layer.

It is naturally not necessary for the invention to consist of a label 119 in accordance with the above description. In alternative embodiments, for example, the layers 145, 146, 147 can be arranged as separate layers one on top of the other on the diaper 101.

It is also possible to imagine the possibility that two of the three layers 145, 146, 147 are joined together before they are applied to the diaper 101. For example, the background layer 146 and the intermediate layer 147 can constitute a combined first component that is attached to the diaper 101 in a first stage, after which the pattern layer 145 containing the pattern 118 is arranged on top of this first component.

Described in U.S. Pat. No. 5,190,812 is a film material that may conceivably be used for the intermediate layer 147 of the label 119. The film material exhibits the characteristic that it is transformed from an essentially transparent state into an essentially opaque state by stretching. The film material also exhibits elastic characteristics, in which case it does not need to be laminated together with any transparent elastic film material before being used in the diaper 101 in accordance with the invention. The film is formed from fibres and consists of one or more elastic layers and one or more layers of non-elastic material.

Heat and pressure under controlled forms are used in accordance with the patent to produce a transparent film that is transformed into an opaque state when it is stretched. The elastic components in the film material exhibit residual elongation not exceeding 20% following elongation by circa 300%-500%.

The opacity is brought about when the non-elastic components of the film material are subjected to plastic deformation during elongation, in conjunction with which the difference in opacity can already be noted after elongation by approximately 5%. These characteristics can be influenced by varying the constituent components in the film material and its thickness. The patent describes suitable components and manufacturing methods for a film material that is suitable for the invention.

Depending on the position of the label 119 on the diaper 101, the intermediate layer 147 of the label 119 must be transformed from its first, essentially transparent state to its second, more opaque state for different elongations, because different parts of the body exhibit different sensitivity to contact pressure. For example, tightening of/contact by the diaper 101 around the waist is less sensitive than excessively tight contact of the inner side leakage barriers 109 with the wearer's groin area. The indication of precise values for the point at which the intermediate layer 147 of the label 119 must be transformed from its first state to its second state must be arrived at by a process of trial and error, because the degree of stretching, in addition to the point on the wearer's abdomen at which contact is produced, will depend on the stretching force exhibited by the elastic element.

U.S. Pat. No. 5,200,247 presents an alternative film material that is transformed from being essentially transparent in its basic state to being essentially opaque when it is stretched. The described film material consists of a mixture of polycaprolacton (PCL) and polyvinyl alcohol (PVA). Films that are produced exclusively with one or other component in the mixture are not opaque when stretched, but in the case of a mixture of the materials, the resulting film material becomes essentially opaque when it is stretched.

Figure 5:
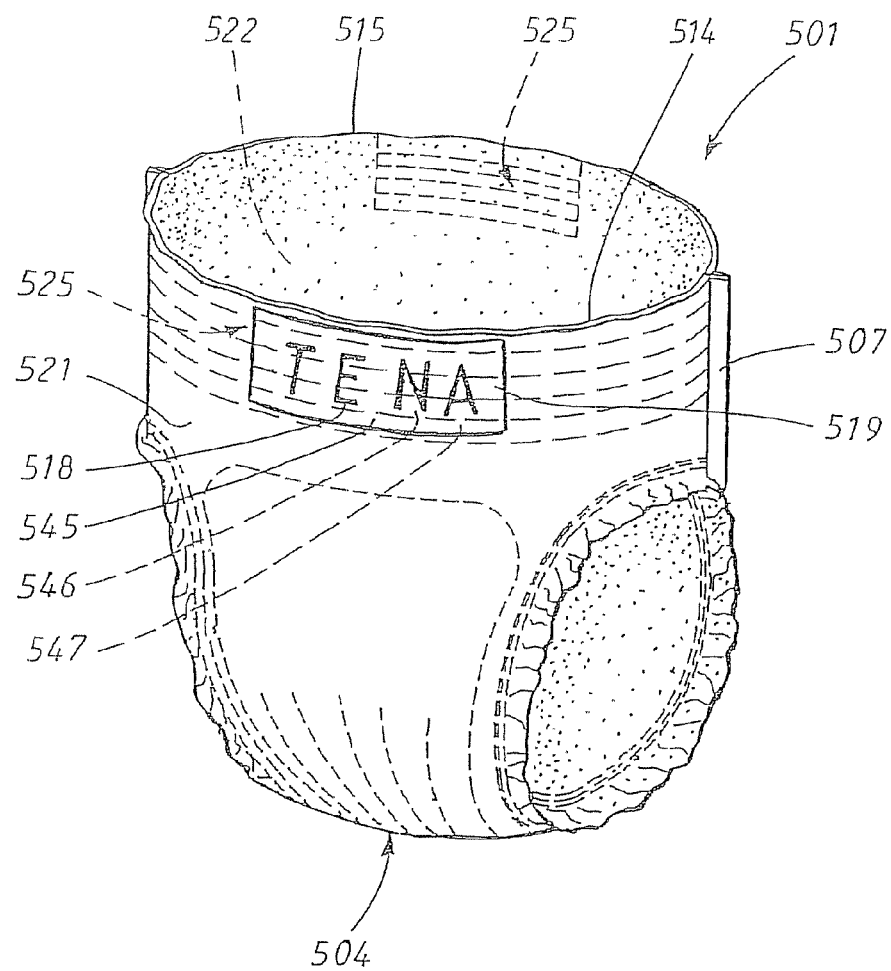
FIG. 5 shows a pant diaper in accordance with an embodiment of the invention.

Examples 1 and 4 in U.S. Pat. No. 5,200,247 describe functional mixtures. FIG. 5 in the same Patent shows how the materials produced in accordance with example 4 reduce the light transmission capacity for an increase in length of 200% (from 6 inches to 18 inches), which increase in length has been achieved by a varying rate of elongation. At a rate of elongation of circa 5 mm/sec, the light transmission capacity of the material is already reduced from circa 85% to circa 20% for one material in the elongation in question. The change in the light transmission capacity of the film material takes place as a consequence of the formation of micro pores and micro cavities when the material is stretched, in conjunction with which the pores/cavities trap the light that would otherwise have passed through. Although the process described in U.S. Pat. No. 5,200,247 relates mainly to the stretching of the layer of material in order to make it opaque before it is applied, for example to an absorbent article, it is obvious that it can be applied in a non-stretched transparent state in view of the statement that the material can be stretched at room temperature in order to cause it to become opaque.

Reference is made to U.S. Pat. No. 5,200,247 in its entirety for a more detailed description of the manufacturing process in its entirety and the components contained in the film. U.S. Pat. No. 5,200,247 is incorporated herein by reference.

A suitable, commercially available film material is marketed by the ACE RKW Film Division in Liege, Belgium, under the product name CODE 728.

Although a description of a few conceivable materials that are suitable for inclusion in the intermediate layer 147 of the label 119 in a diaper 101 in accordance with the invention is given above, a person skilled in the art will readily appreciate that these materials can be replaced by other materials exhibiting the same effect. The essential nature of the invention is such that the characteristics of the material must satisfy the requirement that it is essentially transparent in its first state, and that the material in a second state, after it has been elongated to a sufficient extent, is at least partially opaque, so that the background layer 146 of the label 119 is essentially concealed, in conjunction with which the pattern becomes visible. The choice of material itself is not of critical significance as long as it cannot be regarded as being injurious to the health or, when other similar factors are taken into consideration, its use in a diaper 101 or some other absorbent article is undesirable.

The opacity value of a layer of material is a measure of the ability of the layer of material visually to conceal, for example, a subjacent text through the layer of material, or, as in the case of the embodiment described here, to conceal the background layer 146 so that the pattern 118 becomes visible.

The opacity is measured as a percentage value, where an opacity of 100% indicates that nothing can be seen through the layer of material, and 0% indicates that the layer of material is fully transparent.

The principle of an opacity measurement involves measuring the light reflectance factor ($R_0$) through a layer of material against a standardized black background, and the intrinsic reflectance factor ($R\infty$) against a bundle of layers of material, in which case the bundle of layers of material is entirely opaque. The opacity is determined according to the formula $100 \times R_0/R\infty$.

The measurements were performed in accordance with the ISO 2471:1998 method, which is originally a method intended for measuring the opacity of white or almost white sheets of paper. However, the method also functions for those types of material that are suitable in the present invention.

The measurements were carried out using a Color Touch 2, model ISO, from Technidyne in the USA, in conjunction with which calibrations were performed in accordance with the manual supplied with the apparatus.

The measured opacity values consist of the mean values for five measurements.

The opacity of the CODE 728 film material from ACE RKW Film Division (Liege, Belgium) was measured in its first, non-stretched state, in conjunction with which the layer of material exhibited an opacity of 48.1%.

The film material was applied as an intermediate layer 147 to the label 119, in conjunction with which the background layer 146 of the label 119 was clearly visible through the intermediate layer 147. Because the pattern 118 that is arranged on the transparent pattern layer 145 exhibits the same shade of colour as the background layer 146, the pattern 118 is essentially invisible when the intermediate layer 147 is in its first state.

The same film material, when stretched by circa 200%, that is to say when it has been transformed into its second state, exhibited an opacity of 76.2%. At this opacity of the intermediate layer 147, the background layer 146 was concealed, in conjunction with which the pattern 118 was visible relatively clearly against the intermediate layer 147.

Stretching of the film material by circa 200% meant that the thickness of the material layer was reduced from 70 μm before stretching to 25 μm after stretching.

In a second measurement, two intermediate layers 147 of the same film material from ACE Film Division were placed one on top of the other, after which the opacity of the double layers was measured. The layers exhibited an opacity of 70.5% in their first state, in conjunction with which the background layer 146 could be seen clearly through the intermediate layer 147, and in conjunction with which the pattern 118 was essentially invisible.

In their second, stretched state, the intermediate layers 147 exhibited a combined opacity of 89.1%. For the purposes of this second measurement, too, the layers were stretched by circa 200% when they were in their second state. The pattern 118 was now very clear because the background layer 146 was very effectively concealed by the two intermediate layers 147.

Figure 2A:
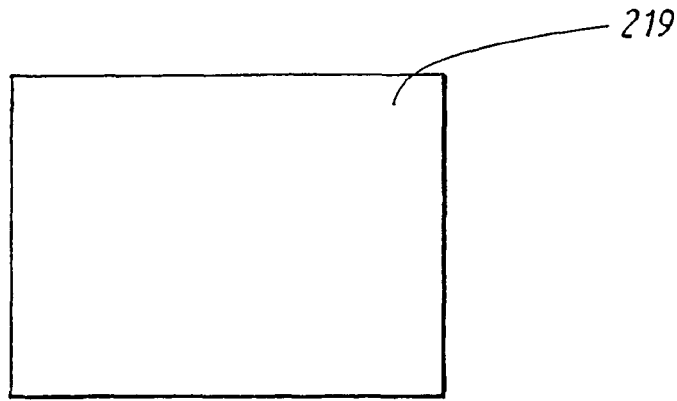
FIG. 2a shows a label constructed in accordance with an embodiment of the invention.

FIG. 2a shows a label 219 of the type described in the illustrative embodiment in accordance with FIGS. 1b and 1c above before the label 219 had been stretched.

Figure 2B:
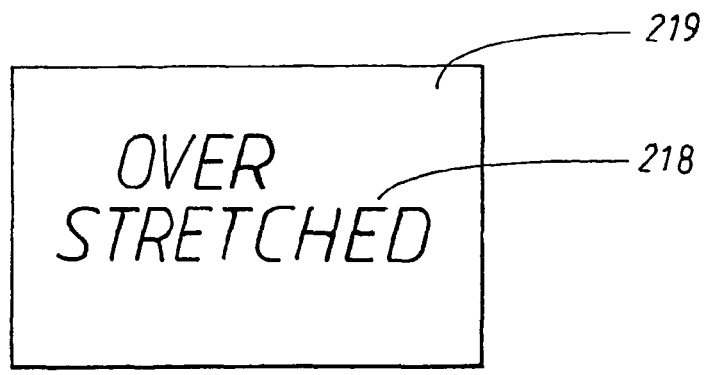
FIG. 2b shows the label in FIG. 2a after it has been stretched.

FIG. 2b shows the label 219 in FIG. 2a after stretching of the label 219.

Figure 2C:
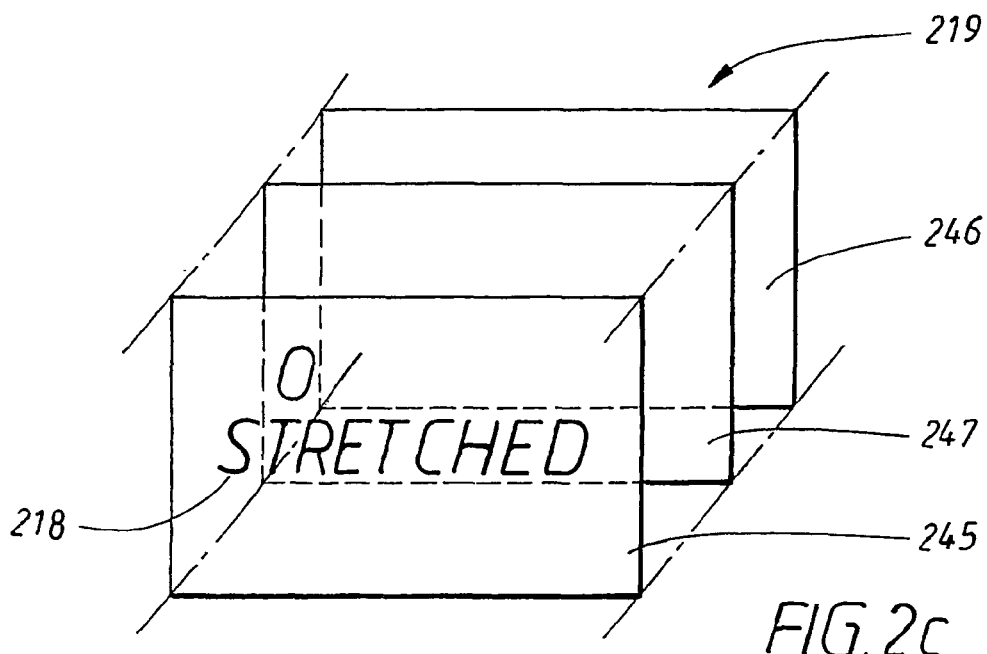
FIG. 2c shows an exploded view of the label in FIGS. 2a and 2b, in conjunction with which the different layers of material in the label are shown.

FIG. 2c shows an exploded view of the construction of the label 219 consisting of three layers and a pattern in the form of the warning text "OVER STRETCHED".

The designations used in FIGS. 2a, 2b and 2c, which have a corresponding designation in FIGS. 1a, 1b and 1c, have the same designation digit in the numerical series 200-299 as the corresponding designation in the numerical series 100-199 in FIGS. 1a, 1b and 1c. For example, the pattern layer has the designation 145 in FIGS. 1b and 1c, and the designation 245 in FIG. 2c.

The label 219 comprises a pattern layer 245, in conjunction with which a pattern 218 in the form of the warning text "OVER STRETCHED" is arranged by means of printing on the pattern layer 245.

The label 219 also comprises a coloured background layer 246, in conjunction with which the shade of colour of the background layer 246 harmonizes with the shade of colour of the printed pattern 218. The pattern 218 and the pattern layer 245 are superimposed on the background layer 246.

A third layer, the so-called intermediate layer 247, is arranged between the pattern layer 245 and the background layer 246. The intermediate layer 247 is characterized primarily in that it can exhibit two different states, a first, essentially transparent state and a second, at least partially opaque state, in conjunction with which the second state is obtained after stretching the label 219 comprising the intermediate layer 247.

The intermediate layer 247 is shown in FIGS. 2a and 2c in its first, essentially transparent state, in conjunction with which the text "OVER STRETCHED" is not visible due to the fact that the background layer 246 exhibits the same shade of colour as the shade of colour of the pattern 218.

In the exploded view shown in FIG. 2c, it can be seen that only the letter "O" in the word "OVER" is visible, due to the fact that the letters "VER" are present in front of the background layer 246 in the exploded view.

In FIG. 2b, the label 219 has been subjected to elongation, in conjunction with which the intermediate layer 247 has been transformed into its second, essentially more opaque state, so that the pattern 218 in the form of the printed warning text "OVER STRETCHED" has become visible.

The pattern layer 245, the background layer 246 and the intermediate layer 247 all have the same length and width and are arranged so that their edges coincide.

In alternative embodiments, it is possible to imagine that the three layers, 245, 246, 247 have different sizes, but it is important for the intermediate layer 247 to cover the entire pattern 218 so that the entire pattern appears after stretching the label.

In other alternative embodiments, it is possible to imagine that the background layer 246 consists of the liquid-impermeable backing layer of the absorbent article, or of its liquid-permeable covering layer, in conjunction with which the shade of colour of the pattern 218 must be adapted in accordance with the layer that constitutes the background layer.

The intermediate layer 247 exhibits its first, essentially transparent state when the label 219 is applied to an absorbent article, in conjunction with which the pattern 218 is not visible against the background layer 246, since the pattern 218 and the background layer 246 exhibit the same shade of colour, and since the intermediate layer 247 is essentially transparent.

When the label 219 is elongated, the intermediate layer 247 is transformed into its second, at least partially opaque state, in conjunction with which the pattern 218 becomes visible against the at least partially opaque intermediate layer 247 which conceals the background layer 246.

The pattern layer 245, the intermediate layer 247 and the background layer 246 are laminated together and together form the label 219.

On the side of the background layer 246 that is intended to face towards an absorbent article, the background layer 246 is already coated with a pressure-sensitive adhesive in conjunction with manufacture of the labels, in which case the labels 219 can be applied directly to absorbent articles without requiring the application of any extra adhesive.

In alternative embodiments, the labels 219 can be supplied to the production machine for absorbent articles without being coated with adhesive, in which case the labels 219 must be coated with adhesive in conjunction with their application to the absorbent articles.

The labels 219 are usually supplied in roll form, in which case individual labels 219 are separated from the roll in conjunction with their application to the absorbent articles.

Figure 3A:
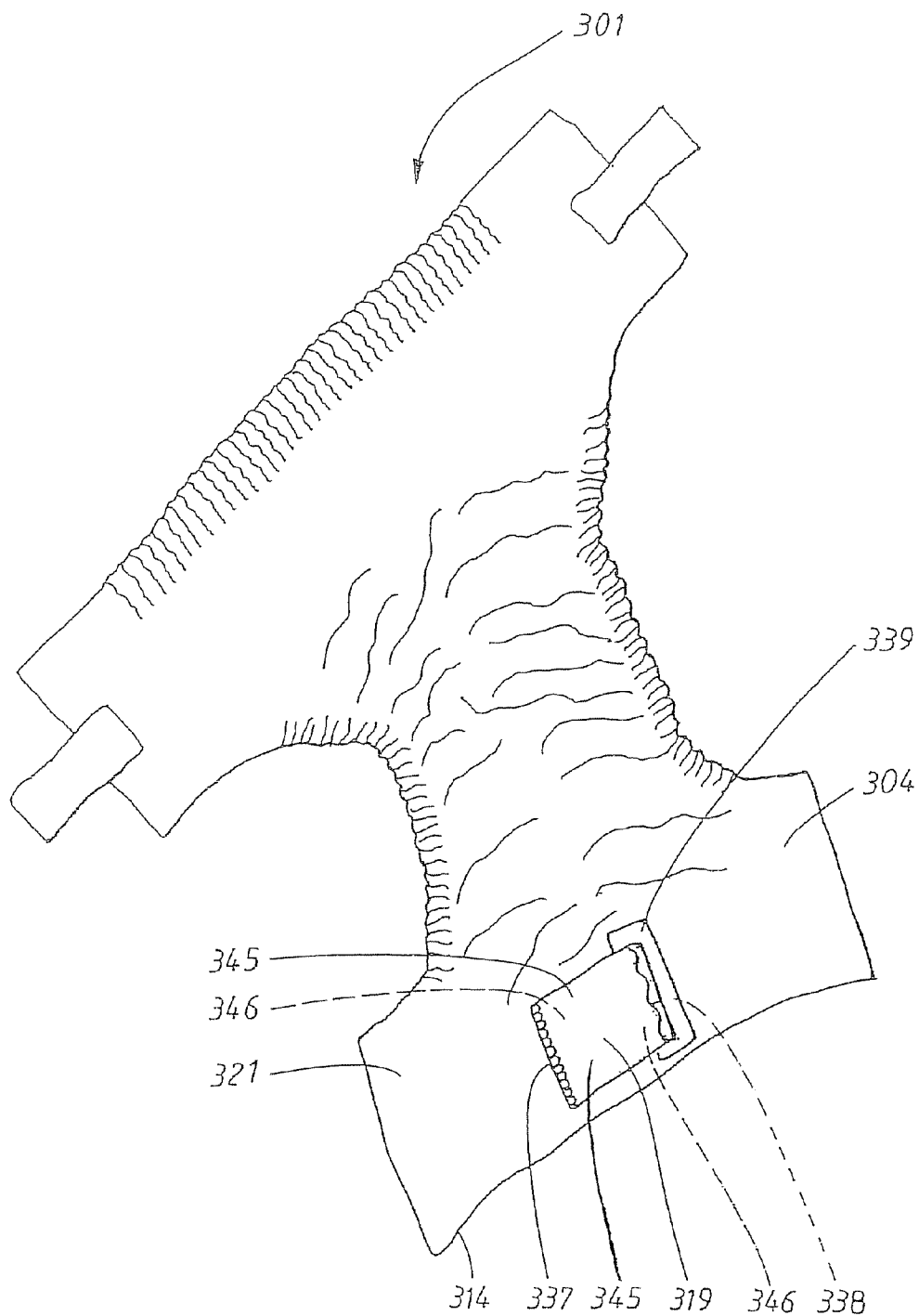
FIG. 3a shows a diaper comprising an alternative embodiment of the invention.
Figure 3B:
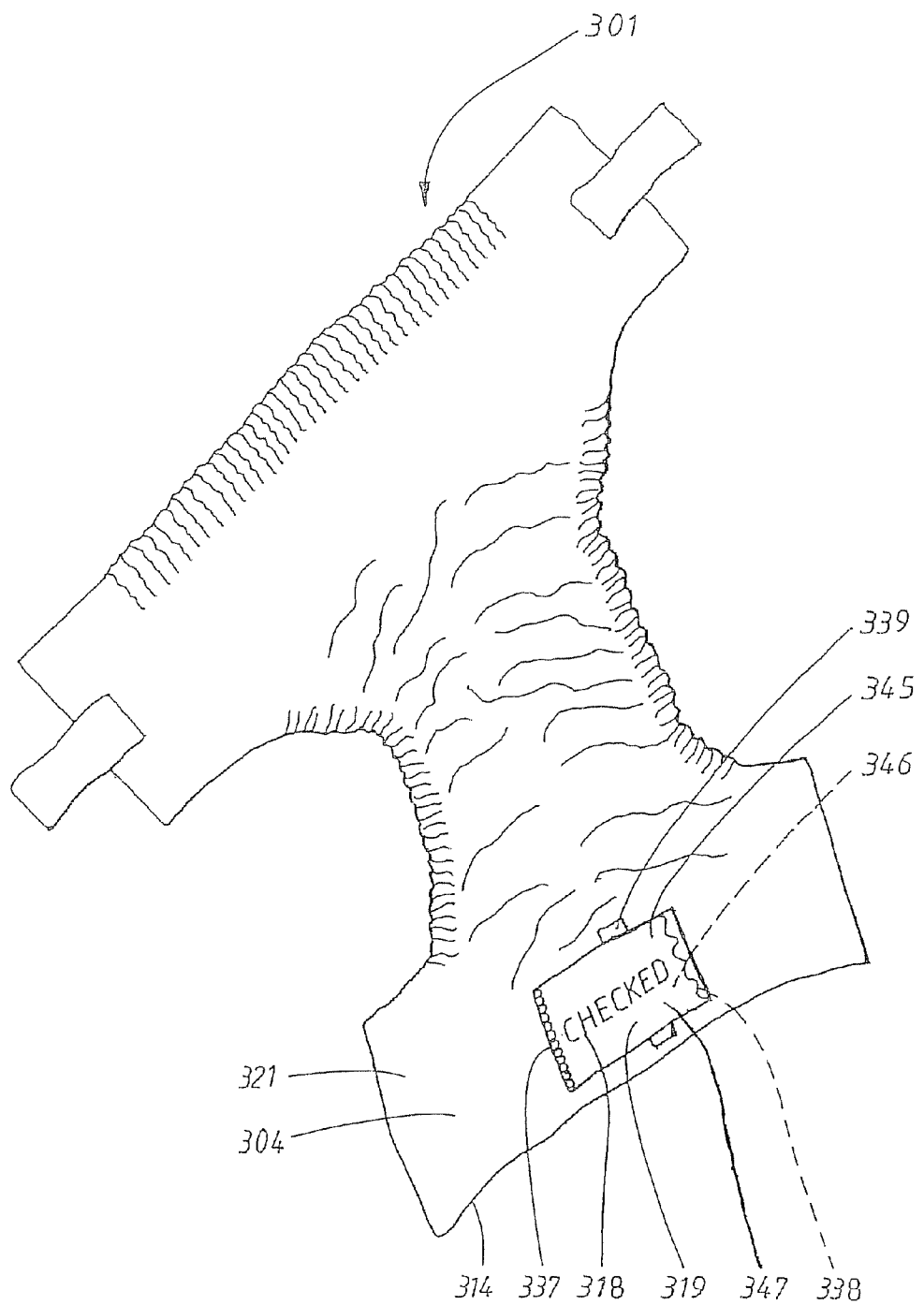
FIG. 3b shows the diaper in FIG. 3a after the label has been stretched manually.

FIGS. 3a and 3b show a diaper 301 in accordance with an alternative embodiment of the invention. The diaper 301 is shown in FIGS. 3a and 3b from the side which, when it is being worn, is intended to face away from the wearer.

The designations used in FIGS. 3a and 3c, which have a corresponding designation in one or other of the preceding figures, have the same designation digit in the numerical series 300-399 as the corresponding designation in the lower numerical series in earlier figures. For example, the pattern layer has the designation 145 in FIGS. 1b and 1c, and the designation 345 in FIG. 3.

The diaper 301 is constructed essentially in the same way as the diaper 101 in FIGS. 1a, 1b and 1c. The diaper 301 is primarily a so-called incontinence diaper intended for adult incontinent wearers, in conjunction with which it is used, for example, in the care of patients on a hospital ward or in a home for the elderly. The provision of such care by its nature involves a number of carers in the care of each individual patient, in conjunction with which a lack of clarity often easily arises in respect of what measures have been taken for a particular patient.

The diaper 301 exhibits a label 319 comprising two layers of material. The two layers of material consist of a background layer 346 arranged closest to the backing layer 304 of the diaper 301, and a pattern layer 345 arranged on the surface of the background layer 346 facing away from the diaper 301.

A pattern 318 is arranged on the pattern layer 345 on the side of the pattern layer 345 that faces away from the diaper 301.

The diaper 301 is characterized first and foremost in that the pattern layer 345 of the label 319 is essentially transparent in a first state and is transformed into an essentially more opaque state when it is elongated.

In this embodiment, the pattern layer 345 of the diaper 301 thus also constitutes the intermediate layer 347 of the diaper 301, in conjunction with which the pattern 318 is arranged on the surface of the pattern layer 345 that faces away from the background layer 346.

The pattern 318 exhibits essentially the same shade of colour as the background layer 346, in conjunction with which the pattern 318 is essentially invisible against the background layer 346 through the pattern layer 345 when this is in its first, essentially transparent state.

When the label 319 is stretched out, the pattern layer 345 is transformed into its second, essentially opaque state, in conjunction with which the pattern 318, which is arranged on the surface of the pattern layer 345 that faces away from the background layer 346, becomes visible.

The pattern 318 consists of the text "CHECKED". The label 319 containing the pattern 318 is arranged in an area of the backing layer 304 that does not exhibit any elastic characteristics.

The label 319 exhibits essentially square form, in conjunction with which two of the edges of the label 319 are arranged essentially parallel to the front transverse edge 314 of the diaper 301.

The label 319 is attached to the backing layer 304 of the diaper 301 along one of the edges of the label 319 that is arranged perpendicular to the front transverse edge 314 of the diaper 301 by means of a permanent ultrasonically welded connection 337.

A separable glued joint 338 connects the opposite edge of the label 319 to a surface 339 that has been treated with a release agent arranged on the backing layer 304.

The glue in the glued joint 338 preferably consists of a pressure-sensitive hot-melt adhesive.

The surface 339 that has been treated with a release agent consists of a siliconized surface arranged on the backing layer 304.

In alternative embodiments, the surface 339 that has been treated with a release agent may consist of a separate piece of material that has been attached to the backing layer 304 of the diaper 301. The piece of material in this case may consist of a sheet of paper siliconized on one side, a waxed paper, an embossed plastic film or the like.

When wearing the diaper 301, it is possible to make the pattern 318 appear manually by separating the separable glued joint 338 in one simple operation and by then elongating the label 319 in the transverse direction of the diaper 301 to such an extent that the pattern layer 345 is transformed into its second, essentially less transparent state. After elongation, the glued joint 338 is again attached to the backing layer 304 of the diaper 301 by means of the pressure-sensitive adhesive. Because the newly created glued joint will not be opened on any subsequent occasion, it is appropriate for the reclosure of the glued joint to be arranged against a surface on the backing layer 304 that has not been treated with a release agent. The diaper 301 with a stretched and resealed label 319 is shown in FIG. 3b, in conjunction with which the pattern 318 is visible.

Diapers 301 containing labels 319 in accordance with this embodiment are, as mentioned above, particularly suitable for use in institutional care, where a number of different carers care for one and the same patient. By stretching out the label 319 so that the pattern 318 is visible, it is possible to indicate to subsequent carers that the diaper 301 has been checked in respect of the content of urine therein, for example. It is naturally also possible to show alternative indications of other measures that have been performed for the patient by means of a label 319 in accordance with the above description.

The label 319 in accordance with the embodiment shown in FIGS. 3a and 3b does not need to be elastic, because it is not intended to interact with any elastic element on the diaper 301, although there is naturally no disadvantage if the label 319 exhibits elastic characteristics.

Figure 4A:
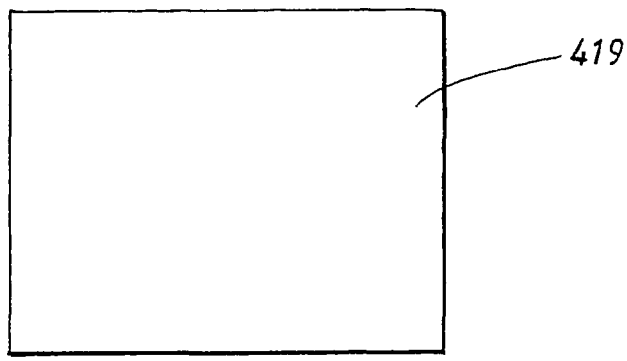
FIG. 4a shows an alternative label in accordance with an embodiment of the invention.

FIG. 4a shows a label 419 of the type described in the illustrative embodiment in accordance with FIGS. 3a and 3b above before the label 419 was stretched out.

Figure 4B:
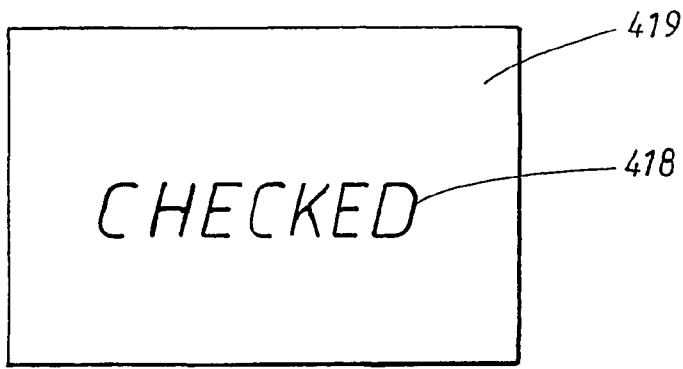
FIG. 4b shows the label in FIG. 4a after it has been stretched.

FIG. 4b shows the label 419 in FIG. 4a after stretching.

Figure 4C:
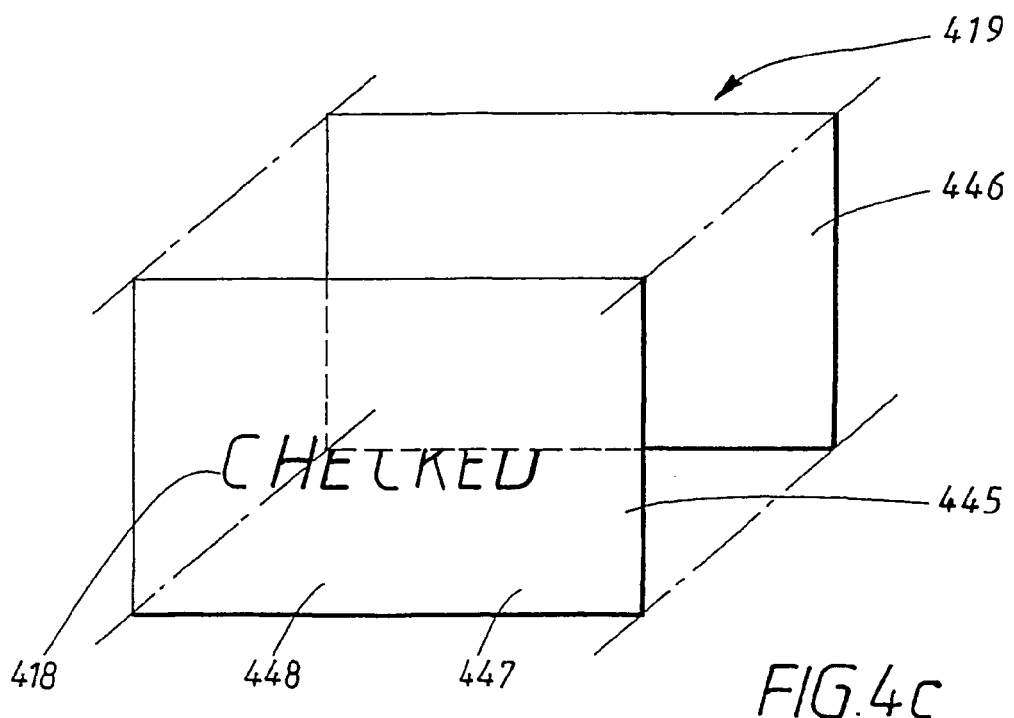
FIG. 4c shows an exploded view of the label in FIGS. 4a and 4b, in conjunction with which the different layers of material in the label are shown.

FIG. 4c shows an exploded view of the construction of the label 419 comprising two layers and a pattern in the form of the text "CHECKED".

The designations used in FIGS. 4a, 4b and 4c, which have a corresponding designation in one or other of the preceding figures, have the same designation digit in the numerical series 400-499 as the corresponding designation in the lower numerical series in earlier figures.

The label 419 comprises a pattern layer 445, which at the same time constitutes the intermediate layer 447 of the label 419, as well as a background layer 446. A pattern 418 in the form of the text "CHECKED" is arranged by means of printing on the pattern layer 445 that faces away from the background layer 446, that is to say on the outward-facing surface 448 of the pattern layer 445.

The shade of colour of the background layer 446 harmonizes with the shade of colour of the superimposed printed pattern 418.

The pattern layer 245 is characterized first and foremost in that it is capable of exhibiting two different states, a first, essentially transparent state and a second, at least partially opaque state, in conjunction with which the second state is obtained after stretching the label 419 containing the pattern layer 445.

The pattern layer 445 is shown in FIGS. 4a and 4c in its first essentially transparent state, in conjunction with which the text "CHECKED" is not visible due to the fact that the background layer 446 exhibits the same shade of colour as the shade of colour of the pattern 418.

In the exploded view shown in FIG. 4c, the letters "CH" are fully visible, while only the bottom half of the letters "ECKED" in the word "CHECKED" are visible. The reason why the top half of the letters "ECKED" are not visible is that they are present in front of the background layer 446, which exhibits the same shade of colour as the shade of colour of the letters, and that the pattern layer 445 is transparent in its first state.

In FIG. 4b, the label 419 has been subjected to elongation, in conjunction with which the pattern layer 445 has been transformed into its second, essentially more opaque state, so that the pattern 418 in the form of the printed text "CHECKED" has become visible.

The pattern layer 445 and the background layer 446 are rectangular, in conjunction with which both layers 445, 446 exhibit the same length and width and are arranged so that their edges coincide.

In alternative embodiments, it is possible to imagine that the label 419 exhibits an alternative form, for example circular form, oval form or the like.

In other alternative embodiments, it is possible to imagine that the background layer 446 consists of the liquid-impermeable backing layer of the absorbent article, or of its liquid-permeable covering layer, in conjunction with which the shade of colour of the pattern 418 must be adapted in accordance with the layer that forms the background layer.

The pattern layer 445 exhibits its first, essentially transparent state when the label 419 is applied to an absorbent article, in conjunction with which the pattern 418 is not visible against the background layer 446, since the pattern 418 and the background layer 446 exhibit the same shade of colour, and since the pattern layer 445 is essentially transparent.

When the label 419 is elongated, the pattern layer 445 is transformed into its second, at least partially opaque state, in conjunction with which the pattern 418 becomes visible because a new shade of background colour has been created in the form of the essentially more opaque intermediate layer 447.

The pattern layer 445 and the background layer 446 are laminated together and together constitute the label 419. This label 419, too, can naturally comprise a pressure-sensitive adhesive on the side which, in conjunction with application, is intended to be attached to an absorbent article, although it can alternatively be supplied without pressure-sensitive adhesive.

FIG. 5 shows a pant diaper 501 intended primarily for incontinent adult users. The designations used in FIG. 5, which have a corresponding designation in one or other of the preceding figures, have the same designation digit in the numerical series 500-599 as the corresponding designation in the lower numerical series in earlier figures. The pant diaper 501, which is shown from the front in a configuration resembling that when it is being worn, is constructed largely in the same way as the open diaper 101 in FIG. 1. The pant diaper 501 differs primarily from the open diaper 101 in FIG. 1 in that the pant diaper 501 is intended to be put on a wearer in the same way as a pair of underpants, that is to say to be passed over the legs. The front end part 521 and the rear end part 522 of the pant diaper 501 have already been connected together in this case in the waist area of the pant diaper 501 during manufacture, in conjunction with which the pant diaper 501 has been given the form of panties.

The waist connection 507 consists of an ultrasonic weld, but in alternative embodiments it can consist of a glued joint, a thermally welded joint, a sewn joint or the like.

It is customary today for pant diapers 501 to be capable of being opened and reclosed, in conjunction with which the connection 507 between the end parts 521, 522 of the pant diaper 501 can be opened to permit inspection of the pant diaper 501 when it is being worn and can then be reclosed so that it can continue to be worn. It is usual in this case for the pant diaper 501 to have been provided with attachment flaps (not shown in the figure), which can be used for reclosing after the prefabricated connection 507 has been separated and rendered unserviceable.

Pant diapers 501 that are capable of being opened, or separated, are also advantageous when the pant diaper 501 must be removed from a wearer after use, in particular if the pant diaper 501 is smeared with faeces. The waist connection 507 of the pant diaper 501 can be separated in this case when it is to be removed from a wearer, so that the contaminated pant diaper 501 does not need to be passed over the wearer's legs and feet during removal.

As far as the positioning of patterns on the pant diaper 501 is concerned, they are usually positioned in appropriate locations corresponding to those indicated for the open diaper 101 in FIG. 1.

Patterns may conceivably be present on the backing layer 504 adjacent to the front transverse edge 514 of the pant diaper 501 and/or adjacent to the rear transverse edge 515 of the pant diaper 501, which form the waist of the pant diaper 501 and where the waist elastic 525 is arranged. It is also conceivable to position patterns in alternative locations on the front and/or rear end part 521, 522 of the pant diaper 501.

The pant diaper 501 is characterized in that it comprises a label 519 comprising a pattern 518 functioning in accordance with the invention. The label 519 is arranged on the waist elastic 525 on the front end part 521 of the pant diaper 501.

The label 519 comprises three material layers. The three material layers consist of a transparent pattern layer 545 arranged furthest away from the diaper 501, a background layer 546 arranged closest to the diaper 501, and an intermediate layer 547 arranged between the pattern layer 545 and the background layer 546. A pattern 518 in the form of the text "TENA" is arranged on the transparent pattern layer 545.

The pant diaper 501 is characterized first and foremost in that the intermediate layer 547 of the label 519 is essentially transparent in a first state, in conjunction with which the pattern 518 is visible against the background layer 546 through the transparent intermediate layer 547, because the background layer 546 and the pattern 518 exhibit essentially different shades of colour. When the intermediate layer 547 is subjected to elongation, the intermediate layer 547 is transformed into a second, essentially less transparent state, in conjunction with which the shade of colour of the intermediate layer 547 changes to a shade of colour that is essentially the same shade of colour as the shade of colour of the pattern 518, in conjunction with which the pattern 518 becomes essentially invisible against the intermediate layer 547.

When the pant diaper 501 is put on a wearer, the pant diaper 501 is stretched around the wearer's waist, especially when the pant diaper 501 is pulled over the wearer's hips. The waist elastic 525 of the pant diaper 501 is stretched out in this case from its initially contracted state, in conjunction with which the label 519 is elongated together with the waist elastic 525.

When the intermediate layer 547 of the label 519 is elongated in conjunction with the application of the pant diaper 501 on a wearer, the intermediate layer 547 is transformed automatically into its second state, in conjunction with which this second state exhibits significantly less transparency compared with the first, non-elongated state. The background layer 546 in this case is essentially concealed by the intermediate layer 547, in conjunction with which the intermediate layer 547 constitutes a new background for the pattern 118.

The shade of colour of the pattern 518 has been selected intentionally so that it harmonizes with the shade of colour of the intermediate layer 547 once this has been transformed into its second, essentially opaque state, in conjunction with which the shades of colour of the pattern 518 and the intermediate layer 547 essentially merge together.

In alternative embodiments, the three layers 545, 546, 547 of the label can naturally be replaced by separate layers which are attached to the pant diaper 501 in the correct sequence.

Figure 6A:
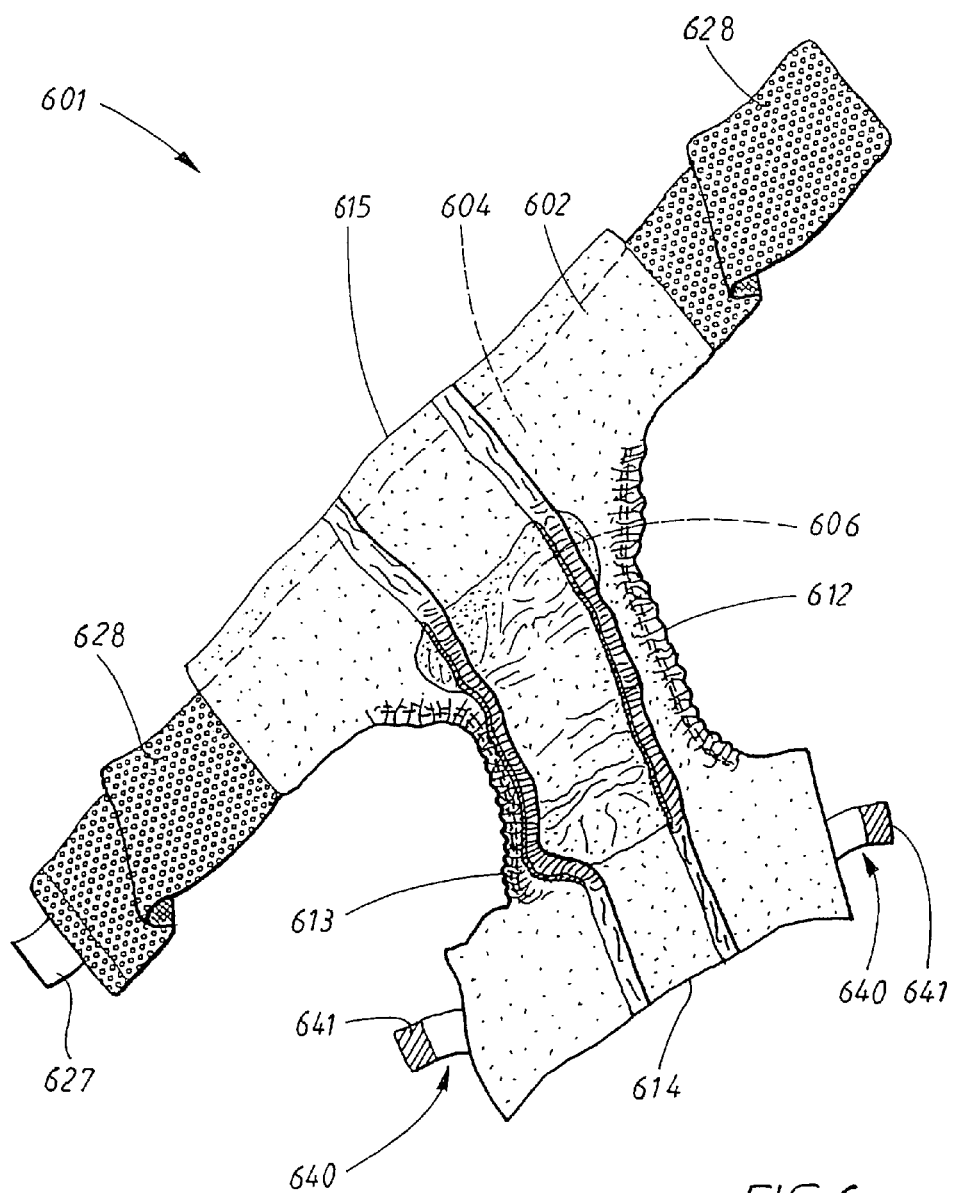
FIG. 6a shows a belt diaper in accordance with an embodiment of the invention from the side that is intended to face towards the wearer when it is being worn.
Figure 6B:
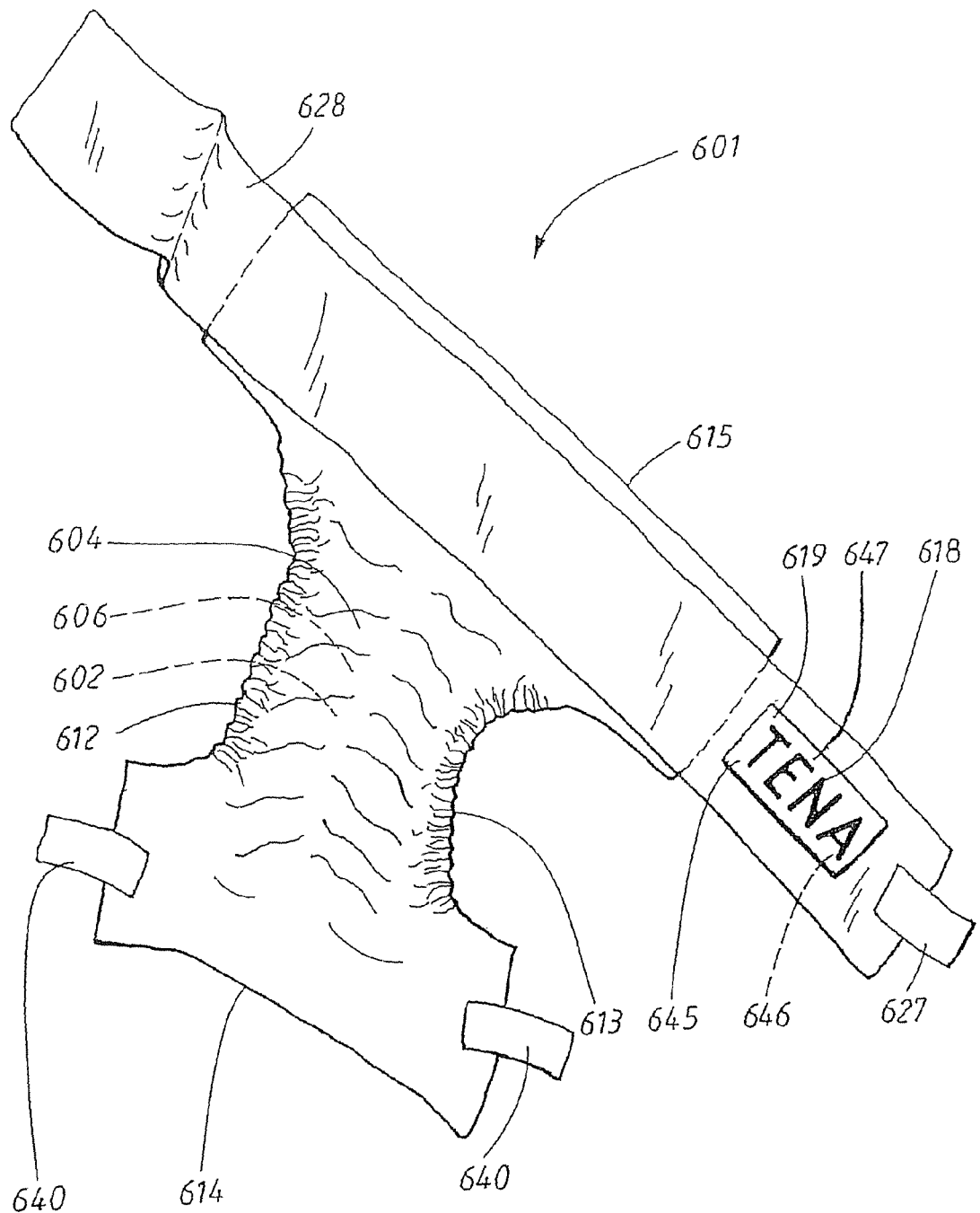
FIG. 6b shows the belt diaper in FIG. 6a from the side that is intended to face away from the wearer when it is being worn.

FIG. 6*a* shows a belt diaper 601 in accordance with the invention from the side which, when it is being worn, is intended to face towards the wearer, and FIG. 6*b* shows the same belt diaper 601 from the opposite side.

The designations used in FIGS. 6*a* and 6*b*, which have a corresponding designation in one or other of the preceding figures, have the same designation digit in the numerical series 600-699 as the corresponding designation in the lower numerical series in earlier figures.

The belt diaper 601 differs from an open diaper in that its attachment arrangement comprises an elastic belt 628 intended to enclose the wearer's waist, in conjunction with which the belt comprises a fixing device 627 for fixing the belt 628 around the wearer's waist.

The belt 628 is attached to a rear transverse edge 615 and extends in a transverse direction in relation to the absorption body 606 of the belt diaper 601.

In alternative embodiments, the belt diaper 601 can comprise two belt halves, in which case the respective half of the belt is joined to the liquid-permeable covering layer 602 and/or the backing layer 604 of the belt diaper 601 on the longitudinal edges 612, 613 of the belt diaper 601 next to the rear transverse edge 615.

The attachment arrangement also comprises two front fixing devices 640 arranged on the longitudinal edges 612, 613 of the belt diaper 601 next to the front transverse edge 614. The front fixing devices 640 are intended to be fixed to the belt 628 in conjunction with the application of the belt diaper 601 to a wearer.

The front fixing devices 640 comprise hook-and-loop elements 641 intended to interact with the side of the belt 628 that is intended to face away from the wearer when the diaper is being worn.

In alternative embodiments, the front fixing devices 640 can comprise adhesive elements intended to be fixed to the surface of the belt 628 facing away from the wearer. The belt 628 in this case must include surfaces intended to interact with the adhesive elements.

When the belt diaper 601 is to be applied to a wearer, the belt 628 is fixed around the wearer's waist as a first stage. The absorption part of the belt diaper 601 comprising, among other things, the front transverse edge 614 and the absorption body 606, is then passed between the wearer's legs, after which two front fixing devices 640 are finally attached to the side of the belt 628 facing away from the wearer.

A label 619 comprising a pattern 618 is arranged on the elastic belt 628 of the belt diaper 601. The label 619 comprises a pattern layer 645 and a background layer 646. The label 619 is attached to the side of the elastic belt 628 that faces away from the wearer when the diaper is being worn, in conjunction with which the background layer 646 faces towards the belt 628.

The belt diaper 601 is characterized first and foremost in that the pattern layer 645 of the label 619 is essentially transparent in a first state, and in that the pattern layer 645 is transformed into an essentially more opaque state when it is subjected to elongation. The pattern layer 645 is thus a layer which constitutes both the pattern layer 645 and the intermediate layer 647 of the belt diaper 601. The pattern 618 is accordingly arranged on the side of the pattern layer 645 that faces away from the background layer 646.

A pattern 618 in the form of the text "TENA" is arranged on the surface of the pattern layer 645 that faces away from the background layer 646, that is to say on the outward-facing surface of the pattern layer 645. The pattern 618 is visible because the pattern 618 and the background layer 646 exhibit different shades of colour, and because the combined pattern layer 645/intermediate layer 647 are in the first, essentially transparent state.

The pattern layer 645 achieves its second state after elongation of the label 619, in conjunction with which elongation occurs in conjunction with the elongation of the belt 628 when it is applied around the wearer's waist.

When the pattern layer 645/intermediate layer 647 is subjected to elongation, it is transformed into its second, essentially less transparent state, in conjunction with which the shade of colour of the pattern layer 645 is changed to a shade of colour which is essentially the same shade of colour as the shade of colour of the pattern 618. The pattern 618 in this case essentially merges with the pattern layer 645, in conjunction with which it becomes essentially invisible.

Elongation is brought about when the belt 628 of the belt diaper 601 is stretched around the wearer in conjunction with putting the belt diaper 601 on the wearer.

The transition from the first, essentially transparent state of the pattern layer 645 to the second, significantly less transparent state thus takes place automatically as a natural part of the application procedure for the belt diaper 601.

The shade of colour of the pattern 618 has been selected intentionally so that it harmonizes with the shade of colour of the pattern layer 645 once this has been transformed into its second, essentially transparent state.

This embodiment means that there is no requirement for a separate layer, the sole purpose of which is to contain the pattern, which reduces the costs relating to the invention.

The label 619 comprising the pattern 618 can naturally be provided with adhesive on the side that is intended to be attached to the belt 628, in conjunction with which no separate adhesive equipment for the attachment of the label 619 is required on the machine which manufactures the belt diapers 601.

A label 619 comprising a pattern 618 can, in alternative belt diapers 601, be positioned on the backing layer 604 in conjunction with the front transverse edge 614. For belt diapers 601 which exhibit two belt halves, it is also conceivable for the pattern 618 to be positioned on the backing layer 604 adjacent to the rear transverse edge 615.

It is also conceivable for patterns 618 to be arranged on labels 619 positioned on the front and/or rear end part of the belt diaper 601 or on the front fixing devices 640.

It is also naturally possible to execute labels consisting of only two layers and an initially visible pattern, where the pattern is essentially rendered invisible manually as described for the diaper 301 in FIGS. 3*a* and 3*b*.

The invention also extends to all conceivable combinations of the described illustrative embodiments.

Furthermore, the invention is not restricted to the above-mentioned illustrative embodiments, but is naturally applicable to other embodiments within the scope of the following patent claims, and equivalents thereof.

The invention claimed is:

1. An absorbent article for disposable use, the article comprising a first layer including at least one pattern formed thereon in a color, wherein in a first mode of the first layer, the first layer is transparent except where the pattern is formed, the first layer superimposed on a background layer, the background layer and the pattern having essentially a same shade of color so that the pattern is not visibly discernable when superimposed over the background layer when the first layer is transparent in the first mode of the first layer; and the absorbent article optionally including an intermediate layer arranged between the pattern and the background layer, the intermediate layer exhibits a first, essentially transparent state in a first mode of the intermediate layer such that the pattern is not visibly discernable against the background layer through the intermediate layer in the first mode of the intermediate layer and when the first layer is in the first mode, and the intermediate layer is caused by elongation to be transformed into a second essentially opaque state in a second mode of the intermediate layer and the first layer remains in the first mode;

wherein if the optional intermediate layer is not included, the first layer is caused by elongation to be transformed into a second essentially opaque state in a second mode of the first layer, such that the pattern is visibly discernable when the first layer exhibits the second, essentially opaque state in the second mode of the first layer except where the pattern is formed.

2. The absorbent article in accordance with claim 1, wherein the intermediate layer, if included, exhibits an essentially different shade of color than the pattern when the intermediate layer exhibits the second, essentially opaque state, such that the pattern is visibly discernable against the intermediate layer when the intermediate layer is in the second mode of the intermediate layer.

3. The absorbent article in accordance with claim 1, wherein the background layer comprises a liquid-permeable covering layer or a backing layer of the article.

4. The absorbent article in accordance with claim 1, wherein, if the intermediate layer is included, the pattern is arranged directly on the intermediate layer, in conjunction with which the pattern is arranged on a side of the intermediate layer that faces away from the background layer.

5. An absorbent article for disposable use, the article comprising:

a background layer;

a layer including at least one pattern formed on the layer, the layer being transparent except where the pattern is formed, the pattern superimposed on the background layer; and at least one intermediate layer arranged between the pattern and the background layer, the at least one intermediate layer exhibits a first, essentially transparent state in a first mode, and the at least one intermediate layer is caused by elongation to be transformed into a second essentially opaque state in a second mode, wherein the pattern and the background layer exhibit essentially different shades of color, such that the pattern is visibly discernable against the background layer through the intermediate layer when the intermediate layer exhibits the first, essentially transparent state in the first mode, and the pattern and the intermediate layer exhibit the same shade of color when the intermediate layer exhibits the second, essentially opaque state in the second mode, such that the pattern is not visibly discernable against the intermediate layer.

6. The absorbent article in accordance with claim 5, wherein the at least one intermediate layer and the layer including the pattern are laminated together and constitute a prefabricated label.

7. The absorbent article in accordance with claim 6, wherein the prefabricated label contains the background layer.

8. The absorbent article in accordance with claim 5, wherein the at least one intermediate layer is attached to an elasticated surface of the article, in conjunction with which the at least one intermediate layer is elongated automatically when the elasticated surface to which it is attached is elongated.

9. The absorbent article in accordance with claim 8, wherein the at least one intermediate layer is arranged in an elasticated waist part of the absorbent article.

10. The absorbent article in accordance with claim 8, wherein the at least one intermediate layer contracts when the elasticated surface to which the at least one intermediate layer is attached contracts.

11. The absorbent article in accordance with claim 5, wherein the at least one intermediate layer is arranged on an elasticated belt of the absorbent article, in conjunction with which the at least one intermediate layer is elongated automatically when the elasticated belt is elongated.

12. The absorbent article in accordance with claim 5, wherein the at least one intermediate layer is arranged on at least one elasticated attachment flap of the absorbent article, in conjunction with which the at least one intermediate layer is elongated automatically when the at least one attachment flap is elongated.

13. The absorbent article in accordance with claim 5, wherein the at least one intermediate layer is intended to be elongated manually in order to cause the at least one intermediate layer to be changed from the first, essentially transparent state to the second, essentially opaque state.

14. The absorbent article in accordance with claim 5, wherein the at least one intermediate layer exhibits a combined opacity of not more than 70.5% in accordance with the method described in ISO 2471:1988 when the at least one intermediate layer is in the first state.

15. The absorbent article in accordance with claim 5, wherein the at least one intermediate layer exhibits a combined opacity of at least 76.2% in accordance with the method described in ISO 2471:1988 when the at least one intermediate layer has been transformed into the second state.

16. The absorbent article in accordance with claim 5, wherein changing the at least one intermediate layer from the first state to the second state is achieved by elongating the at least one intermediate layer by 10-200%.

17. The absorbent article in accordance with claim 5, wherein transition of the at least one intermediate layer from the first, essentially transparent state to the second, at least partially opaque state is irreversible.

18. An absorbent article for disposable use, the article comprising at least one pattern of a color, the pattern superimposed on a background layer having essentially a same shade of color as the at least one pattern, and at least one layer arranged over the background layer, the at least one layer exhibits a first, essentially transparent state in a first mode such that the pattern is not visibly discernable against the background layer through the at least one layer when the at least one layer exhibits the first, essentially transparent state in the first mode, and the at least one layer is caused by elongation to be transformed into a second, essentially opaque state in a second mode such that the pattern is visibly discernable against the at least one layer when the at least one layer exhibits the second, essentially opaque state in the second mode.

19. An absorbent article for disposable use, the article comprising at least one pattern of a color arranged on a surface of a pattern layer, the pattern layer including an intermediate layer and being superimposed on a background layer having a different shade of color than the color of the at least one pattern, the pattern layer exhibiting a first, essentially transparent state in a first mode in which the pattern layer is essentially transparent except where the pattern is arranged such that the at least one pattern is visibly discernable against the background layer through the pattern layer in the first mode, and the pattern layer is caused by elongation to be transformed into a second state in a second mode in which the pattern layer exhibits a color that is essentially the same as the color of the at least one pattern such that the pattern is not visibly discernable against the pattern layer in the second mode.

20. An absorbent article for disposable use, the article comprising:
- a top layer having a pattern of a color on it;
- a background layer of the same color as the pattern; wherein the pattern is superimposed on the background layer; and
- optionally, a third layer arranged between the top layer and the background layer;
- at least one of the top and third layers exhibits a first, essentially transparent state in a first mode of the to layer and third layers, respectively, the transparent state of the top layer being a state where the top layer is essentially transparent except where the pattern is provided, and the at least one of the top and third layers is caused by elongation to be transformed into a second essentially opaque state in a second mode of the top layer and third layers, respectively;
- wherein the transformation of the at least one of the top and third layers affects whether an appearance of the pattern is visibly discernable.

* * * * *